United States Patent [19]

Tsitlik et al.

[11] Patent Number: 5,217,010
[45] Date of Patent: Jun. 8, 1993

[54] ECG AMPLIFIER AND CARDIAC PACEMAKER FOR USE DURING MAGNETIC RESONANCE IMAGING

[75] Inventors: Joshua E. Tsitlik, Reisterstown; Howard Levin, Cockeysville; Henry Halperin; Myron Weisfeldt, both of Baltimore, all of Md.

[73] Assignee: The Johns Hopkins University, Baltimore, Md.

[21] Appl. No.: 706,250

[22] Filed: May 28, 1991

[51] Int. Cl.⁵ .............................................. A61N 1/37
[52] U.S. Cl. .............................. 128/419 PG; 128/696
[58] Field of Search ........................... 128/696, 419 P

[56] References Cited

U.S. PATENT DOCUMENTS

| | | | |
|---|---|---|---|
| 3,881,493 | 5/1975 | Cannon | 128/419 PG |
| 4,038,990 | 8/1977 | Thompson | 128/419 PG |
| 4,248,237 | 2/1981 | Kenny | 128/419 P |
| 4,254,775 | 10/1981 | Langer | 128/419 P |
| 4,436,093 | 3/1984 | Belt | 128/419 PG |
| 4,456,786 | 6/1984 | Kyle | 128/419 P |
| 4,887,609 | 12/1989 | Cole, Jr. | 128/696 |
| 4,899,760 | 2/1990 | Jaeb et al. | 128/696 |
| 4,951,672 | 8/1990 | Buchwald et al. | 128/696 |
| 4,991,580 | 2/1991 | Moore | 128/696 |

FOREIGN PATENT DOCUMENTS 0132785 3/1985 European Pat. Off. ............. 128/696

Primary Examiner—William E. Kamm
Attorney, Agent, or Firm—Howard W. Califano

[57] ABSTRACT

A device for monitoring a patient or pacing a patient is disclosed which can safely operate in a MRI system. The device uses unique RF filtering and shielding to attenuate voltages on the leads resulting from the high frequency RF signals produced in the MRI. The device is uniquely shielded to prevent induced currents from disrupting the amplifying and processing electronics. The device uses an optional secondary low pass or band reject filter to eliminate interference from the MRI's gradient magnetic field. The device uses optional inductors placed close to electrodes to limit RF currents through the electrodes. Several embodiments of the RF filter are taught which depend on the number of sensing leads, whether the leads are shielded, whether the RF filter is contained in the electronic shielded housing or whether single or multistage filtering is employed. The device may operate as an extended ECG monitor or may be an implantable MRI safe pacemaker.

38 Claims, 17 Drawing Sheets

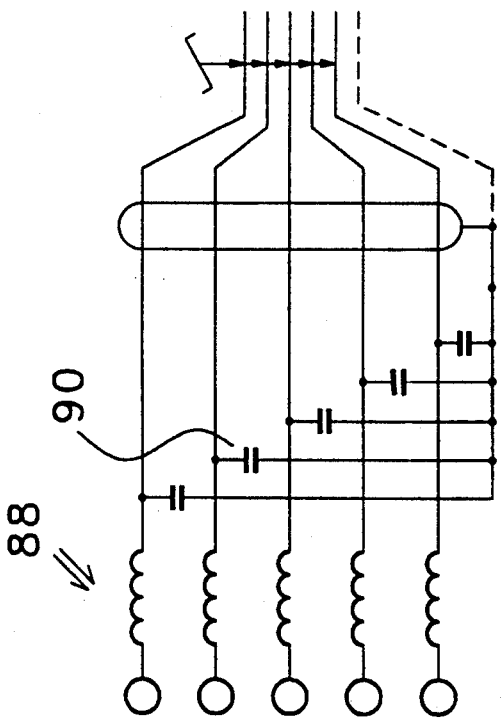
FIG.4b
FIG.4d
FIG.4f
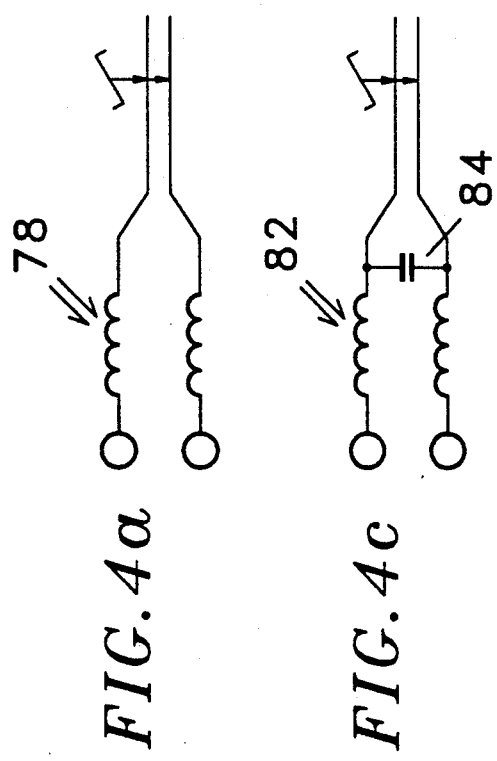
FIG.4a
FIG.4c
FIG.4e

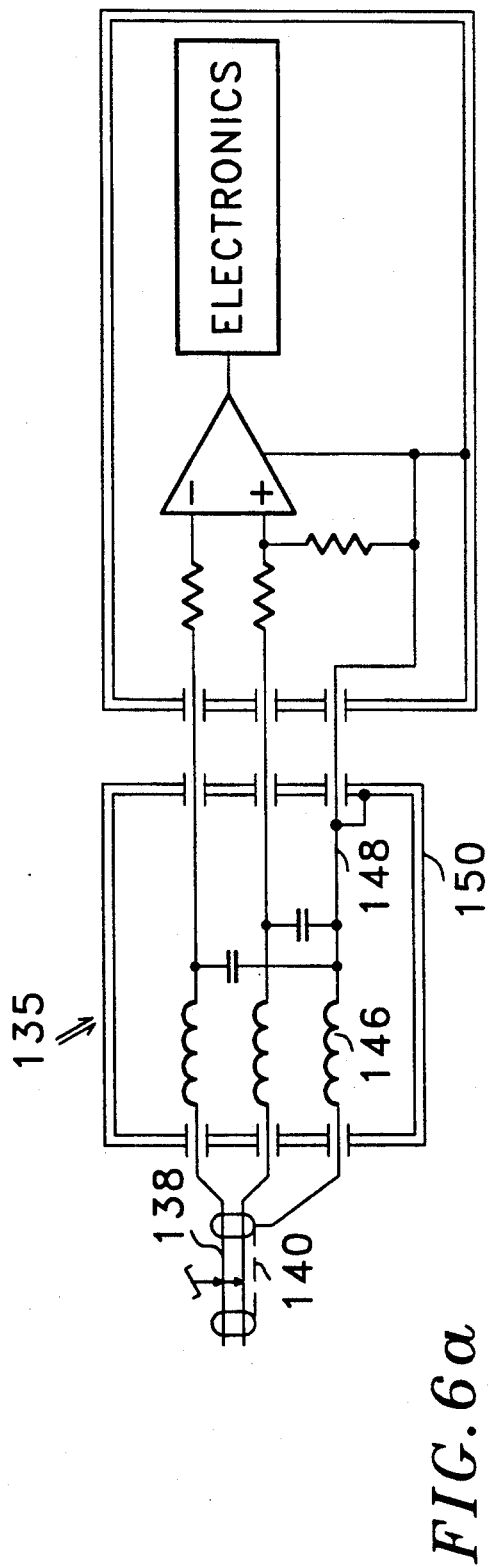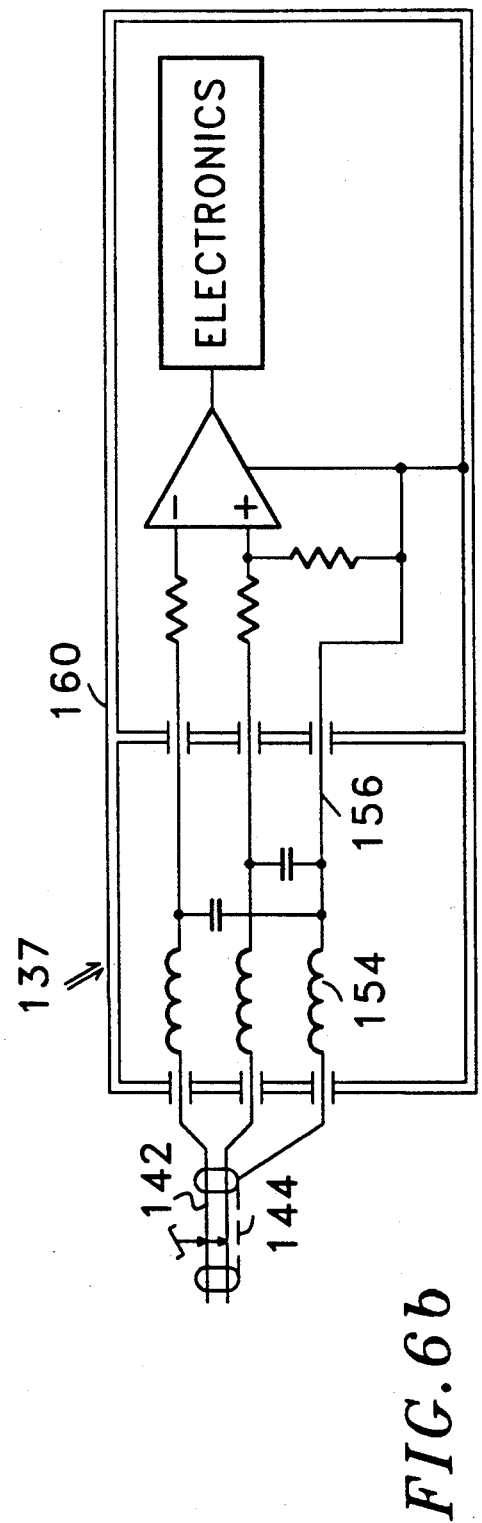
FIG. 6a
FIG. 6b

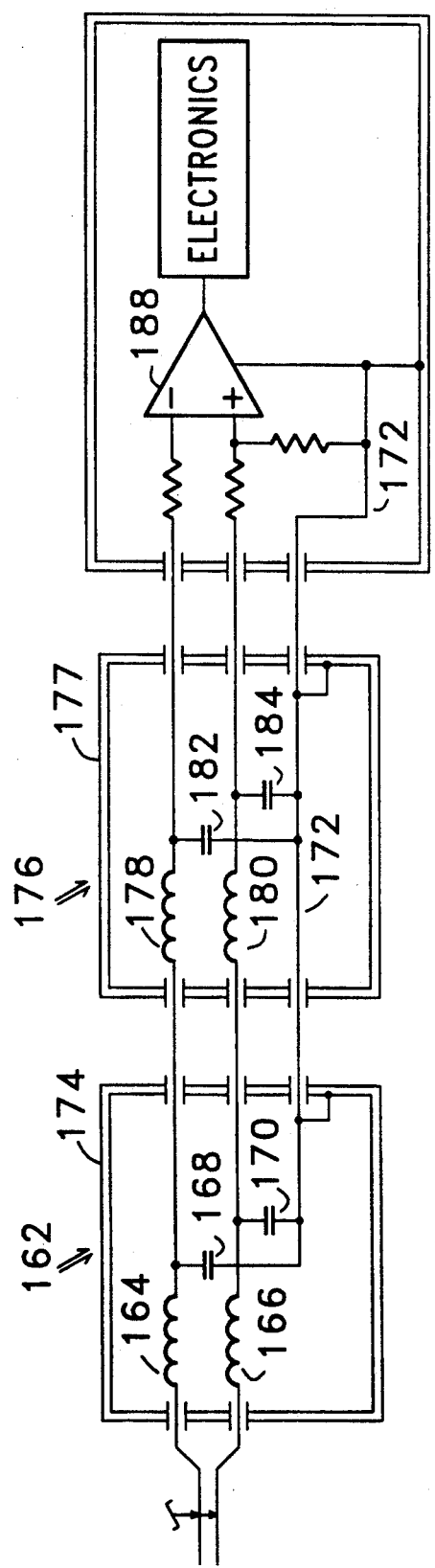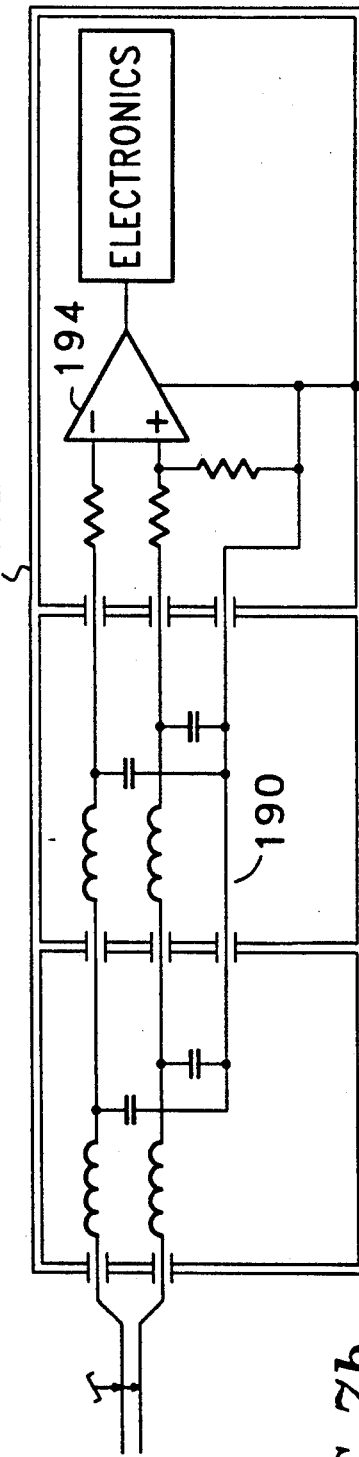
FIG.7a
FIG.7b

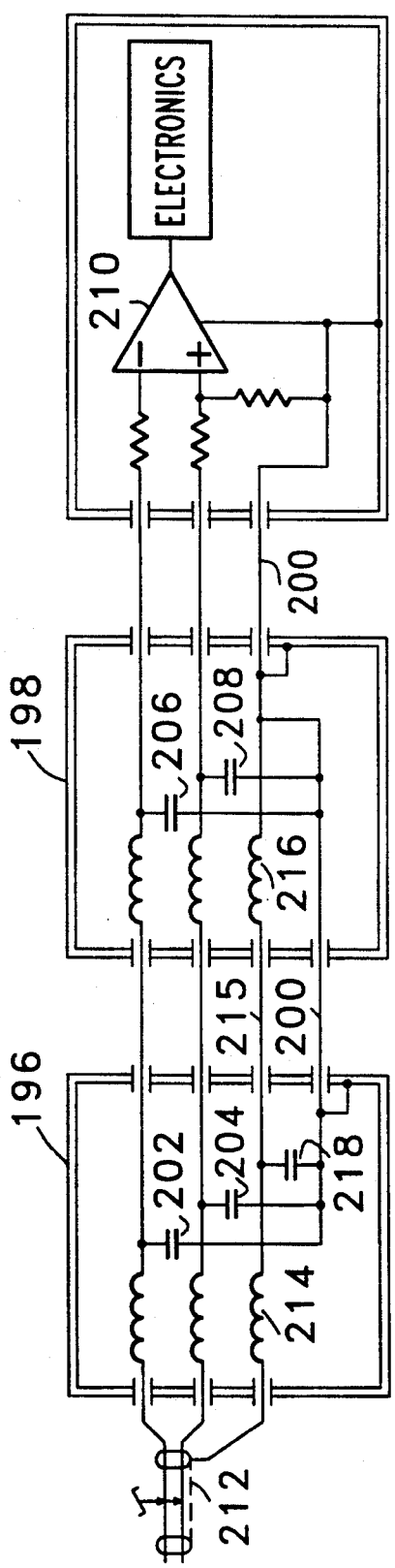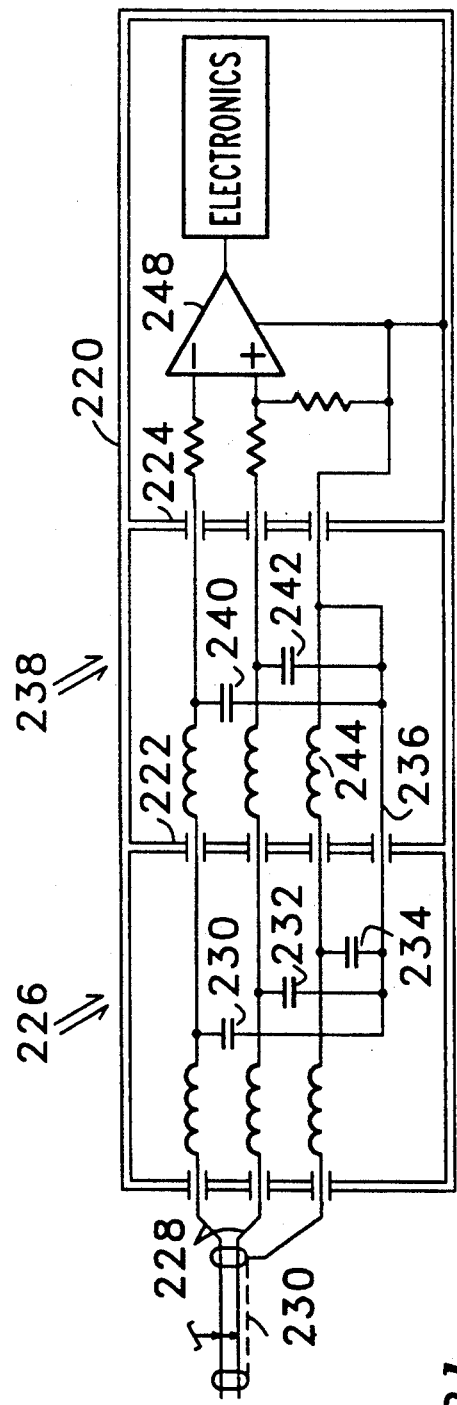
FIG. 8a
FIG. 8b

ECG AMPLIFIER AND CARDIAC PACEMAKER FOR USE DURING MAGNETIC RESONANCE IMAGING

BACKGROUND OF THE INVENTION

1. Field of the Invention

The present invention relates to both implantable and external pacemakers and monitors that may be used in an environment of the high static and radio frequency (RF) magnetic field strength generated by magnetic resonance imaging (MRI) systems.

2. Description of the Prior Art

Pacemakers are commonly used to control the heart rate when there is a disorder of the heart rhythm. However, other types of pacemakers, or tissue stimulators, can be used for pain relief, by local nerve stimulation, or for pacing skeletal muscle in handicapped patients. One new type of pacemaker is used to pace both the cardiac and skeletal muscle for patients who undergo cardiomyoplasty. (Cardiomyoplasty is the placement of a skeletal muscle graft on the heart to assist the failing heart.)

Modern pacemakers perform two functions-ECG sensing (input) and cardiac pacing (output). The ECG signal is monitored via one or two electrodes placed on the epicardial or endocardial surface of the heart or the surface of the body. These ECG sensing electrodes are usually connected to a differential amplifier that increases the low level (1 to 10 mV) ECG signal to a higher level (1 V or larger) signal that can be used by the pacing logic. The pacing logic controls pacemaker operation. Depending on the type of pacemaker and the heart chamber from which the electrical activity is sensed, the pacing output amplifier can be either triggered or inhibited. Noise in the ECG signal from any source can interfere with the proper functioning of the pacemaker. The common sources of noise include muscle artifact, electromagnetic field of power lines, and RF noise from electrocautery. Prior art pacemakers are built to exclude this noise.

Magnetic resonance imaging (MRI) is a new and efficient technique used in the diagnosis of many disorders, including neurological and cardiac abnormalities. MRI has achieved prominence in both the research and clinical arenas. It provides a non-invasive method for the examination of internal structure and function. For example, MRI allows one to study the overall function of the heart in three dimensions significantly better than any other imaging method. More recently, MRI imaging with "tagging" permits the non-invasive study of regional ventricular function.

Until now, however, there has been a reluctance to place patients with pacemakers in an MRI apparatus. The environment produced in the MRI apparatus is considered hostile to pacing electronics. The major risk to patients is pacemaker malfunction caused by the electromagnetic fields produced in the MRI system. MRI systems utilize three types of electromagnetic fields: 1) a strong static magnetic field, 2) a time-varying gradient field; and 3) a radiofrequency (RF) field which consists of RF pulses used to produce an image. The static field utilized by current MRI systems has a magnetic induction ranging from 0.5 to 1.5 T. The frequency of the RF field used for imaging is related to the magnitude of the static magnetic field. For the current generation of MRI systems, the frequency of the RF field ranges from 6.4 to 64 MHz. The time-varying gradient field is used in MRI for spatial encoding. The frequency of this field is in the Kilohertz range.

It was originally feared that the static field would create longitudinal forces and torque on the pacemaker case and leads (P. L. Davis, L. Crooks, M. Arakawa, R. McRee, L. Kaufman, A. R. Margulis. Potential hazards in NMR imaging: Heating effects of changing magnetic fields and RF fields on small metallic implants. AJR 137:857–860, 1981.) However, in the case that was reported, no physical damages to the leads, pacemaker or patient could be attributed to the static field. The patient did not complain of mechanical discomfort (B. H. Zimmermann, D. D. Faul. Artifacts and hazards in NMR imaging due to metal implants and cardiac pacemakers. Diagn. Imag. Clin. Med. 53:53–56, 1984.) However, the static magnetic field can affect the magnetically controlled (reed) switch that prevents inappropriate programming of the pacemaker. When the head of the pacemaker programming unit is placed over the pacemaker, the permanent magnet in the programmer head causes the reed switch to close. The pacemaker is then placed in an asynchronous, or safety, pacing mode while programming takes place. When the pacemaker in placed in the MRI, the reed switch is actuated by the static magnetic field forcing the pacemaker to the asynchronous pacing mode (J. A. Erlebacher, P. T. Cahill, F. Pannizzo, R. J. R. Knowles. Effect of magnetic resonance imaging on DDD pacemakers. Am. J. Cardiol. 57:437–440, 1986; J. Fetter, G. Aram, D. R. Holmes, Jr., J. E. Gray, D. L. Hayes. The effect of nuclear magnetic resonance imagers on external and implantable pulse generators. Pace 7:720–727, 1984; D. L. Hayes, D. R. Holmes, Jr., J. E. Gray. Effect of 1.5 tesla nuclear magnetic resonance imaging scanner on implanted permanent pacemaker. JACC, 10:782–786, 1987.) For a pacemaker to work in the MRI environment, it should not contain a reed switch. However, this then requires a new method of programming not taught in the prior art.

It has been thought by many investigators that the time-varying gradient fields do not effect the proper functioning of the pacemaker (J. A. Erlebacher, P. T. Cahill, F. Pannizzo, R. J. R. Knowles. Effect of magnetic resonance imaging on DDD pacemakers. AM. J. Cardiol. 57:437–440, 1986; D. L. Hayes, D. H. Holmes, Jr., J. E. Gray. Effect of 1.5 tesla nuclear magnetic resonance imaging scanner on implanted permanent pacemaker. JACC, 10:782–786, 1987; F. Iberer, E. Justich, W. Stenzl, H. Machler, K. H. Tscheliessnig, J. Kapeller. Nuclear magnetic resonance imaging of a patient with implantable transvenous pacemaker. Herz-Schrittmacher, MZV-EBM Verlage 7:196–199 1987.) However, contrary to what the prior art taught, the present inventors discovered that the time-varying gradient field can generate significant voltage in the ECG leads that may be interpreted by the ECG amplifier as a QRS complex.

The RF field produced in the MRI system represents a form of electromagnetic interference (EMI) that is very hazardous to the pacemaker. The RF pulses can produce two distinct categories of problems: 1) heating, and 2) voltage generation in the pacemaker, its circuitry and leads.

Heating is the result of eddy currents formed in the metal case of the pacemaker. The conductivity of the tissue surrounding the pacemaker can expand the current path to the tissue. No evidence of abnormal heat generation by the pacemaker was reported in patients (F. Iberer, E. Justich, W. Stenzl, H. Machler, K. H. Tscheliessnig, J. Kapeller. Nuclear magnetic resonance imaging of a patient with implantable transvenous pacemaker. Herz-Schrittmacher, MZV-EBM Verlage 7:196-199 1987.) However, new techniques, such as "tagging", that requires increased number of RF pulses may result in increased heat production.

Voltage generated by the RF pulses has been implicated in two general types of pacemaker malfunction: 1) inhibition of pacing; and, 2) excessively rapid pacing. Both of these malfunctions can result in a life-threatening reduction in blood pressure (D. L. Hayes, D. H. Holmes, Jr., J. E. Gray. Effect of 1.5 tesla nuclear magnetic resonance imaging scanner on implanted permanent pacemaker. JACC, 10:782-786, 1987; J. A. Erlebacher, P. T. Cahill, F. Pannizzo, R. J. R. Knowles. Effect of magnetic resonance imaging on DDD pacemakers. AM. J. Cardiol. 57:437-440, 1986; J. Fetter, G. Aram, D. R. Holmes, Jr., J. E. Gray, D. L. Hayes. The effect of nuclear magnetic resonance imagers on external and implantable pulse generators. Pace 7:720-727, 1984; B. H. Zimmermann, D. D. Faul. Artifacts and hazards in NMR imaging due to metal implants and cardiac pacemakers. Diag. Imag. Clin. Med. 53:53-56, 1984.) As previously noted, a pacemaker placed in a static magnetic field reverts to an asynchronous pacing mode. It has been observed, however, that RF pulses generated by the MRI interfere with this safety mode by totally inhibiting the output of the pacemaker. This inhibition of pacing is especially of concern in those patients totally pacemaker dependent. It has also been observed that the RF pulses produced by the MRI system can pace the heart at rates of up to 800/min (J. A. Erlebacher, P. T. Cahill, F. Pannizzo, R. J. R. Knowles. Effect of magnetic resonance imaging on DDD pacemakers. AM. J. Cardiol. 57:437-440, 1986; D. L. Hayes, D. H. Holmes, Jr., J. E. Gray. Effect of 1.5 tesla nuclear magnetic resonance imaging scanner on implanted permanent pacemakers. JACC, 10:782-786, 1987).

Each of the above pacemaker malfunctions is caused by the generation of unwanted voltages in the pacemaker. These unwanted voltages are generated in the pacemaker in the following manner. The leads, electrodes and tissue between electrodes comprise a winding in which the RF field generates electromotive force (EMF). In an MRI system operating at 6.4 Mhz, voltages of up to 20 V peak-to-peak are generated. In unipolar pacemakers where the case acts as the second electrode, the tissue between the intracardiac electrode and the pacemaker case serve as the second lead providing a winding with a large effective area. Even higher unwanted voltages can be detected in such unipolar pacemakers. The EMF generated in the leads by the MRI system is proportional to the frequency of the RF. At the higher RF frequencies expected for the next generation of MRI systems voltages approaching 100 V may be expected.

Pacemakers as taught in the prior art have some EMI/RF protection (B. H. Zimmermann, D. D. Faul. Artifacts and hazards in NMR imaging due to metal implants and cardiac pacemakers. Diag. Imag. Clin. Med. 53:53-56, 1984). It is clear, however, that this filtering is insufficient. When placed in the MRI environment, these prior art pacemakers fail by the following mechanisms:

a) RF pulses propagate along the pacing leads and are delivered directly to the input and output circuitry of the pacemaker. The RF is transmitted directly via the leads into the pacemaker case itself. Once the RF is inside the case, this voltage can propagate along the pacemaker circuitry causing many different types of malfunction, including inhibition or improper pacing.

b) Second, once the RF enters the pacemaker, the pacemaker circuitry may act as a rectifier and demodulator of the EMF. The demodulated signal has a shape similar to a pacing spike and is of significant voltage. Since the output impedance of the output circuitry is low, high current can be produced through the pacing lead. This can result in pacing of the heart with each RF pulse.

The frequencies of RF used for MRI systems require more rigorous methods of noise protection than taught in the prior art. There are two general methods of filtering RF noise—passive and active. Active filters use an operational amplifier and require external power. This method, however, may not be suitable as the primary means of filtering RF. The high voltages generated at the input terminals of the filter by MRI systems (25-100 V as compared to the ECG signal of a few millivolts) can cause the amplifier circuitry to become saturated and severely degrade its performance. On the other hand, passive filters are attractive because they can operate without being saturated by the RF field. One common method of passive filtering in ECG monitors is the use of high resistance to limit current generated by the RF field (U.S. Pat. No. 4,280,507 issued to Rosenberg on Jul. 28, 1981 and U.S. Pat. No. 4,951,672 issued to Buchwald, et al. on Aug. 28, 1990). However, this method is not usable in pacing leads because it limits battery life.

Filters using inductances and capacitances have been previously used in ECG monitors (U.S. Pat. No. 4,245,649 issued to Schmidt-Andersen on Jan. 2, 1981) and pacemakers (U.S. Pat. No. 3,968,802 issued to Ballis on Jul. 13, 1976). These filters were used to protect the monitor and/or pacemaker from RF fields generated during electrocautery, but would not protect the pacemaker in the MRI environment. The circuit elements used in these designs may not function properly at the higher frequencies used by MRIs as the elements appear to have unsuitable frequency characteristics. Further, the inductors used had iron cores (U.S. Pat. No. 4,245,649 issued to Schmidt-Andersen on Jan. 2, 1981). If used in an MRI system, these inductors can be saturated by the high static magnetic field of the MRI, thus lowering their inductance and making their characteristics non-linear. Also, if the ferromagnetic elements are positioned close to the volume being imaged, these elements distort the magnetic field, thus degrading the quality of image and even making the imaging impossible. In addition, the prior art filters, as taught in the above patents, do not filter the lead connected to the ECG reference electrode as well as the shield of the ECG leads and will, therefore, draw the RF noise into the amplifier. Therefore, these prior art filters will not function in the MRI environment.

U.S. Pat. No. 4,887,760 issued to Cole on Dec. 19, 1989 describes a method of filtering an ECG monitor specifically for use in the MRI environment. The filter contains an active element that provides cutoff switching from 50 Hz to 5 Hz when the MRI system is activated. When activated, this filter blocks the RF field, but will also totally block the ECG signal while the MRI imaging sequence is in progress. Since this lockout of the ECG input can last up to two seconds, the monitor could fail to detect a QRS complex for one or more cycles. Though improving the quality of MRI imaging, this method more than doubles the total imaging time. More importantly, the method has limited utility for pacemakers because inhibition of ECG sensing can lead to life-threatening complications.

SUMMARY OF THE INVENTION

The inventors overcame problems not addressed by the prior art and invented a generic ECG amplifier and a pacemaker that function normally in the MRI environment. The present invention has application for both implantable and external pacemakers, as well as external ECG monitors. In particular, the invented pacemaker can perform safe and proper sensing of the intracardiac ECG and safe and proper pacing of the heart. External ECG monitors designed according to the present invention can safely and properly monitor and detect ECG signals in the MRI environment using external leads. Such external monitors can be used to synchronize MRI imaging to the ECG signal. This improves data quality and shortens the time necessary for MRI data acquisition. In addition, it allows the safe monitoring of patients undergoing MRI. The present invention has application to other types of pacemakers or stimulators, including but not limited to, implantable or external nerve or tissue stimulation.

In order to operate safely in the MRI environment, the present inventors had to substantially modify the prior art pacemaker design. First, a unique RF filter had to be invented that would serve four purposes. First, the RF filter had to prevent the development of excess voltage on the ECG input amplifier. As discussed previously, the RF field induced by the MRI system generates high voltage signals on the input leads that can saturate or destroy the input amplifier. Secondly, the RF filter had to prevent the generation of excessive electrical current through the ECG electrodes that could potentially induce a dangerous heart rhythm. Thirdly, the RF pulses developed by the MRI system had to be attenuated so that they do not trigger the pacing circuit to stimulate the heart at too rapid a rate, resulting in life-threatening reduction in blood pressure. Fourthly, the RF filter must not interfere with proper sensing of the ECG signal.

The lead or harness design for the monitor/pacemaker also had to be modified. Significant stray capacitance is present along the lead wire system. As a result, EMF generated in the ECG leads because of the MRI system's RF field can produce high currents through the electrodes that are potentially dangerous to the patient. The present inventors placed inductor elements in the leads near the electrodes to attenuate this current and an additional capacitor to improve filter characteristics for the purpose of ECG monitoring, but which does not effect the pacing output.

The present invention also protects the pacemaker from false triggering by the voltage generated in the leads by the gradient field of the MRI. This is accomplished by placing a band reject filter or a low pass filter after the initial amplifier stage that is designed to pass the lower frequency QRS signal and reject the gradient field frequencies that are approximately 1-50 kHz.

The present inventors also had to develop RF shielding enclosures for two purposes. First, each RF filter stage must be shielded from the other filter stages and from the pacing circuitry. Secondary emission from the components of the RF filter would induce currents in other filter stages or in the processing electronics unless separately shielded. A new laminated enclosure, for an implantable pacemaker, was designed to reduce heat generation by eddy currents produced by the RF field generated by the MRI system. Since the control electronics for the invented pacemaker is located in the RF shielded enclosure, a new telemetry system had to be developed to transmit control signals to the pacemaker.

Several embodiments of the invented ECG monitor and pacemaker are taught in this specification. These embodiments each utilize modifications of the invented RF filter to accommodate different types of leads, different types of pacing, and different types of shielding enclosures. The filter design as taught by the present inventors has the following elements: 1) each lead as well as the shield of the leads are separately filtered by low pass-filters; 2) each low-pass filter is referenced by its capacitor to a common reference line which originates inside the shielding enclosure of the low-pass filters; 3) each filter stage should be surrounded by a separate shielding enclosure (whether a single case is used with separated compartments or whether separate enclosures are used for each stage); 4) the common reference line is connected to the zero-signal reference terminal of the differential amplifier and is always connected to the amplifier shielding enclosure. (The differential amplifier may contain a single amplifier or multiple amplifiers, in addition the common reference may connect to a driven-right-leg circuit or other arrangement, which are well known common-mode interference reducing arrangements for a differential amplifier circuit. (J. D. Webster, ed.: "Medical Instrumentation, Application and Design", Houghton Mifflin Company, Boston, 1978, pp. 302-303.)) If separate enclosures are used for each stage, the common reference line is connected to each shielding enclosure; if a single case is employed the common reference line is preferably connected to the shielding enclosure at a single point; 5) the inductor and capacitor elements which make up the low-pass filter are high frequency elements, retaining their desired properties up to 100 MHz; and 6) each low-pass filter must be designed to attenuate the high frequency RF emissions produced by the MRI system (in the range of 6-100 MHz) and pass the lower frequency desired physiological signals. The signal generated by the gradient field is filtered by an additional low-pass or band reject filter.

BRIEF DESCRIPTION OF DRAWINGS

FIGS. 4a-4f are schematic drawings of various ECG lead and/or harness configurations designed for operation in the environment produced by an MRI system.

FIGS. 6a and 6b are block diagrams of ECG amplifiers with a one-stage RF filter design, as taught by the present invention, for use with dual shielded leads.

FIGS. 7a and 7b are block diagrams of ECG amplifiers with a multistage RF filter design, as taught by the present invention, for use with dual unshielded leads.

FIGS. 8a and 8b are block diagrams of ECG amplifiers with a multistage RF filter design, as taught by the present invention, for use with dual shielded leads.

FIGS. 10a and 10b show voltages recorded from three ECG electrodes placed on the body surface while the subject is being exposed to RF imaging pulses only: FIG. 10a shows the signal before the invented RF filtering is used (signal is dominated by voltages induced by MRI imaging pulses); and, FIG. 10b shows the QRS signal appearing after the invented RF filtering is used.

FIGS. 11a and 11b show voltages recorded from two ECG electrodes attached to the left ventricle surface while the subject is being exposed to RF imaging pulses only: FIG. 11a shows the signal before the invented RF filtering is used (signal is dominated by voltages induced by MRI imaging pulses); and, FIG. 11b shows the epicardial electrocardiogram appearing after the invented RF filtering is used.

FIGS. 12a and 12b show voltages recorded from two ECG electrodes attached to the left ventricle surface while the subject is being exposed to RF and gradient pulses: FIG. 12a shows the signal before the RF filtering is used (signal is dominated by voltages induced by MRI tagging and imaging pulses); and, FIG. 12b shows the epicardial electrocardiogram appearing after the invented RF filtering is used.

FIGS. 13a, 13b and 13c show voltages recorded from three ECG electrodes placed on the body surface while the subject is being exposed to RF and gradient pulses: FIG. 13a shows the signal before the RF filtering is used (signal is dominated by voltages induced by MRI tagging and imaging pulses); FIG. 13b shows the QRS signal after the invented RF filtering is used (spikes caused by MRI gradient field remain); and, FIG. 13c shows the QRS signal after additional low-pass filtering as taught by the present invention.

DETAILED DESCRIPTION OF PREFERRED EMBODIMENTS

Figure 1:
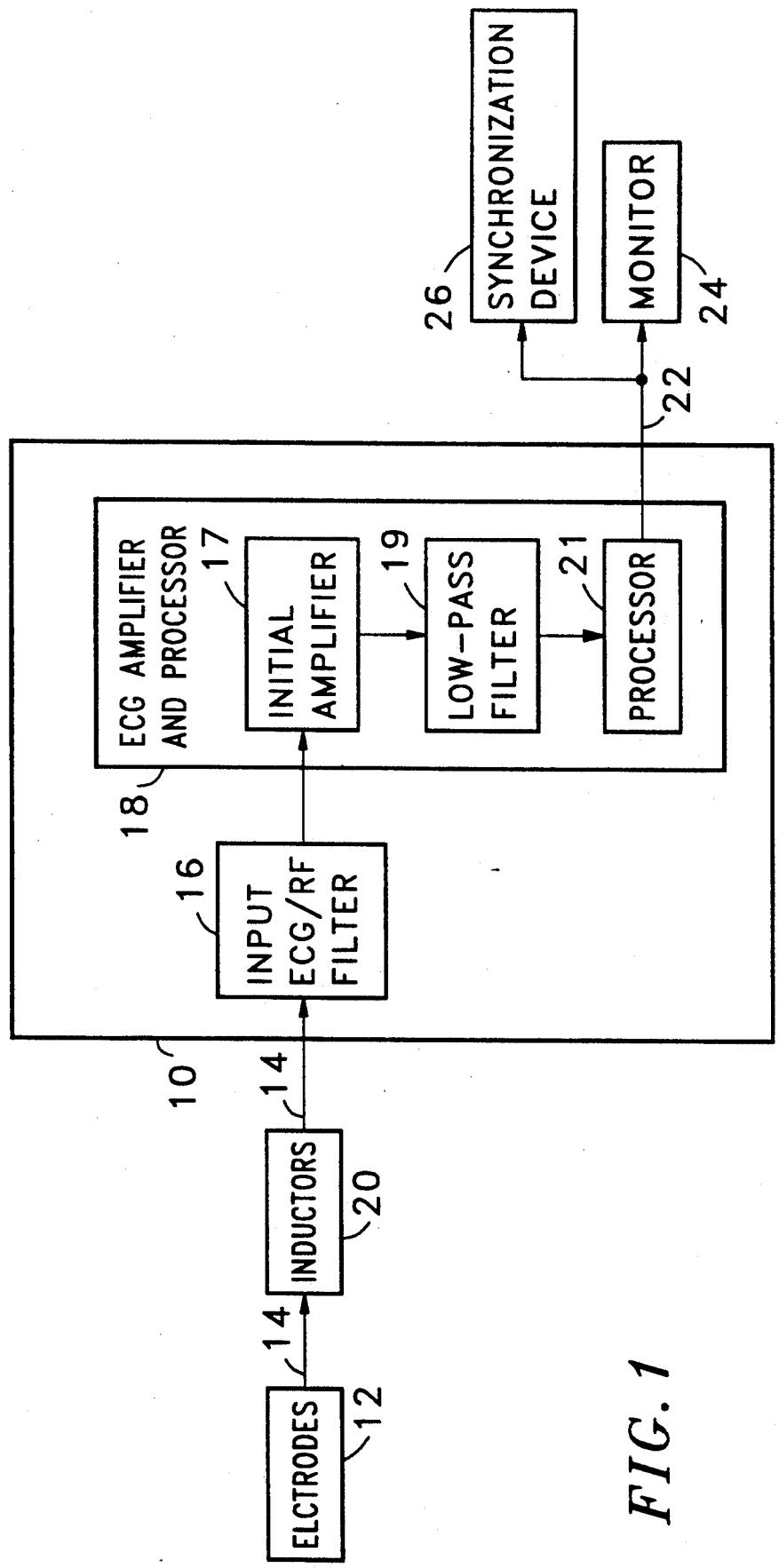
FIG. 1 is a block diagram of an invented ECG amplifier capable of operating in the high static magnetic field, RF field and gradient field environment produced in an MRI system.

A block diagram of an ECG acquisition and processing system, as taught by the present invention, is shown in FIG. 1. The ECG monitoring system can be used as a stand-alone ECG monitor or as part of an external or internal pacemaker. A patient is connected to ECG monitoring circuitry 10 via surface or internal electrodes 12 and lead wires 14. The lead wires 14 connect to the input ECG/RF filter 16. This novel filter design enables the monitoring circuit to operate in the high RF field environment generated by the MRI system. First, the RF filter prevents the development of excess voltage on the ECG input amplifier and processor 18 that would otherwise damage the amplifier. Second, it prevents the development of excess current on the ECG electrodes 12 that would potentially induce a dangerous heart rhythm. Third, the RF filter 16 when attached between the lead wires 14 and the ECG input amplifier will not interfere with proper sensing of the ECG signal. The input ECG/RF filter 16, which will be described in greater detail in this specification, has the characteristics of a low-pass filter with approximately a 100 dB signal attenuation in the commonly used MRI system RF frequency range, which is currently 6–100 MHz. The frequencies contained in the intracardiac or surface ECG signal, however, are passed without any attenuation. In the case where the lead wires 14 are of long length, such as in external monitoring, there is significant stray capacitance between the lead wires. As a result, EMF generated between the electrodes 12 can produce dangerously high current flow through the electrodes. To limit this current, inductors 20, may be placed in the lead wires 14, close to the electrodes.

The ECG/RF input filter 16 and lead wire inductors 20 must contain components with a resonance frequency higher than the RF frequency of the MRI system in use. In addition, all components that are exposed to the static magnetic field (i.e., inductors, capacitors, RF filter) should not contain ferromagnetic materials. The high strength of the static magnetic field produced by the MRI system will saturate the magnetic core of ferromagnetic components, rendering them useless. The ECG amplifier and processor 18 contains low-pass or band reject filter 19 placed after the initial amplifier 17 and before final stages 21. The low-pass or band reject filter must pass the QRS signals and reject gradient field frequencies that are approximately 1–50 kHz. The output ECG signal 22, which can take any conventional form such as an R-wave detector output or analog ECG, can be used for any purpose. It can be used to display the ECG on monitor 24, or synchronize an external or internal device 26, such as an MRI system or cardiac pacemaker.

Figure 2:
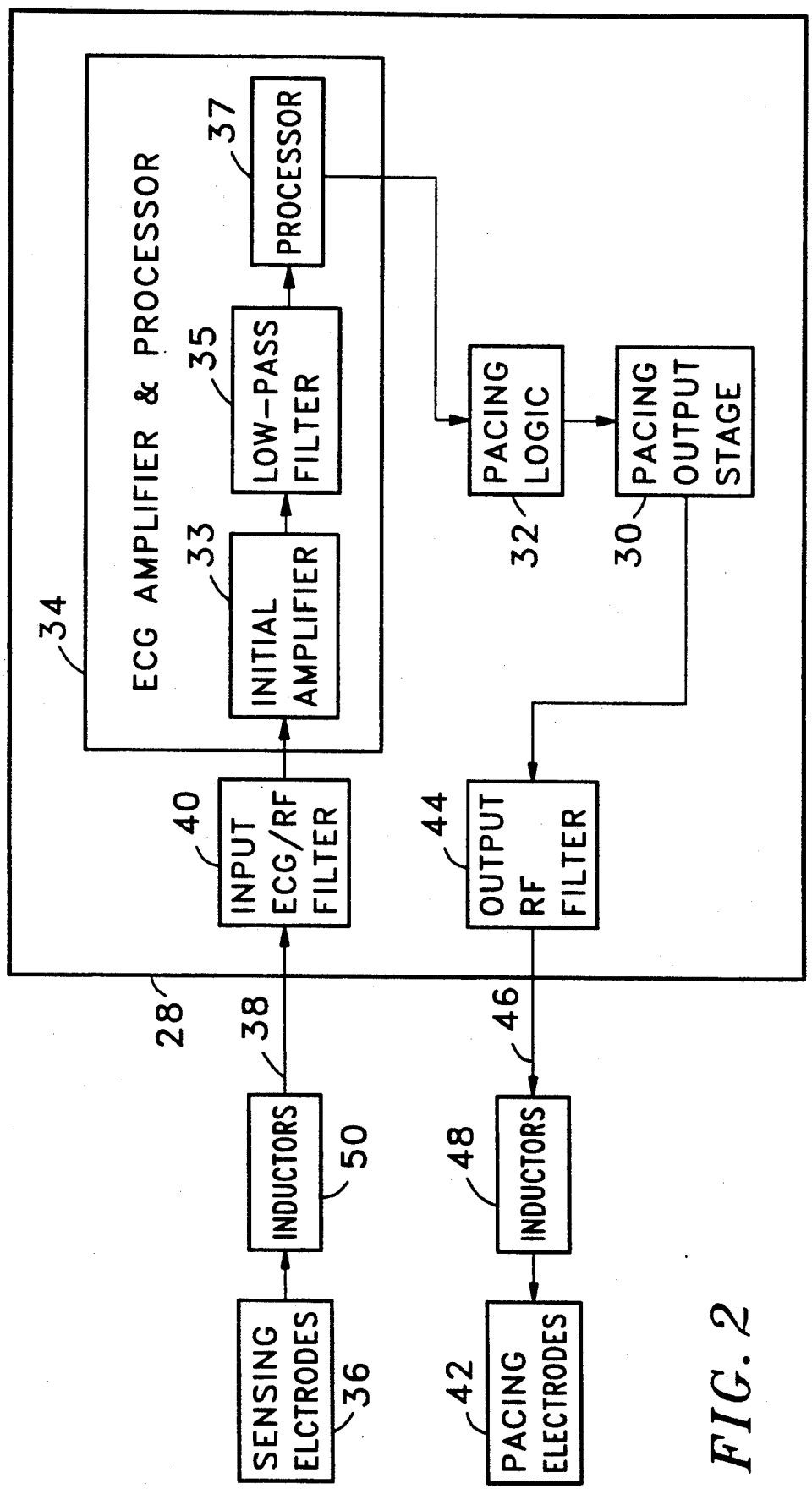
FIG. 2 is a block diagram of an invented pacemaker capable of operating in the high static magnetic fields, RF field and gradient field environment produced in an MRI system.

In another embodiment shown in FIG. 2, a pacemaker system 28 is described. This pacemaker system can be either external or implantable. In addition to the elements shown in FIG. 1, this embodiment also contains a pacing output stage 30 that is controlled by the pacing logic 32. The pacing logic is itself controlled by signals from the ECG amplifier and processor 34. The patient is connected to the pacemaker system 28, via surface or internal sensing electrodes 36 and lead wires 38. The lead wires are connected to the ECG amplifier and processor 34, via the input ECG/RF filter 40. The pacing output stage 30 is connected to pacing electrodes 42 via the output RF filter 44 and pacing lead wires 46. The ECG amplifier and processor 34 contains a low-pass or band reject filter 35 placed after the initial amplifier 33 and before the final stages 37. The low-pass or band reject filter must pass the QRS signal and reject gradient field frequencies caused by the MRI that are approximately 1–50 kHz. As in the previous embodiment, inductors 48, 50 may be placed in the lead wires 38, 46 close to the electrodes 36, 42. In this embodiment of the invention, the sensing 36 and pacing 42 electrodes, wires 38, 46, inductors 48, 50 and RF filters 40, 44 are shown separately. However, these components (as subsequently shown in FIGS. 3, 14 and 15) can be merged to create a combined ECG sensing/pacing RF electrodes, wires, inductors and filters.

Figure 3:
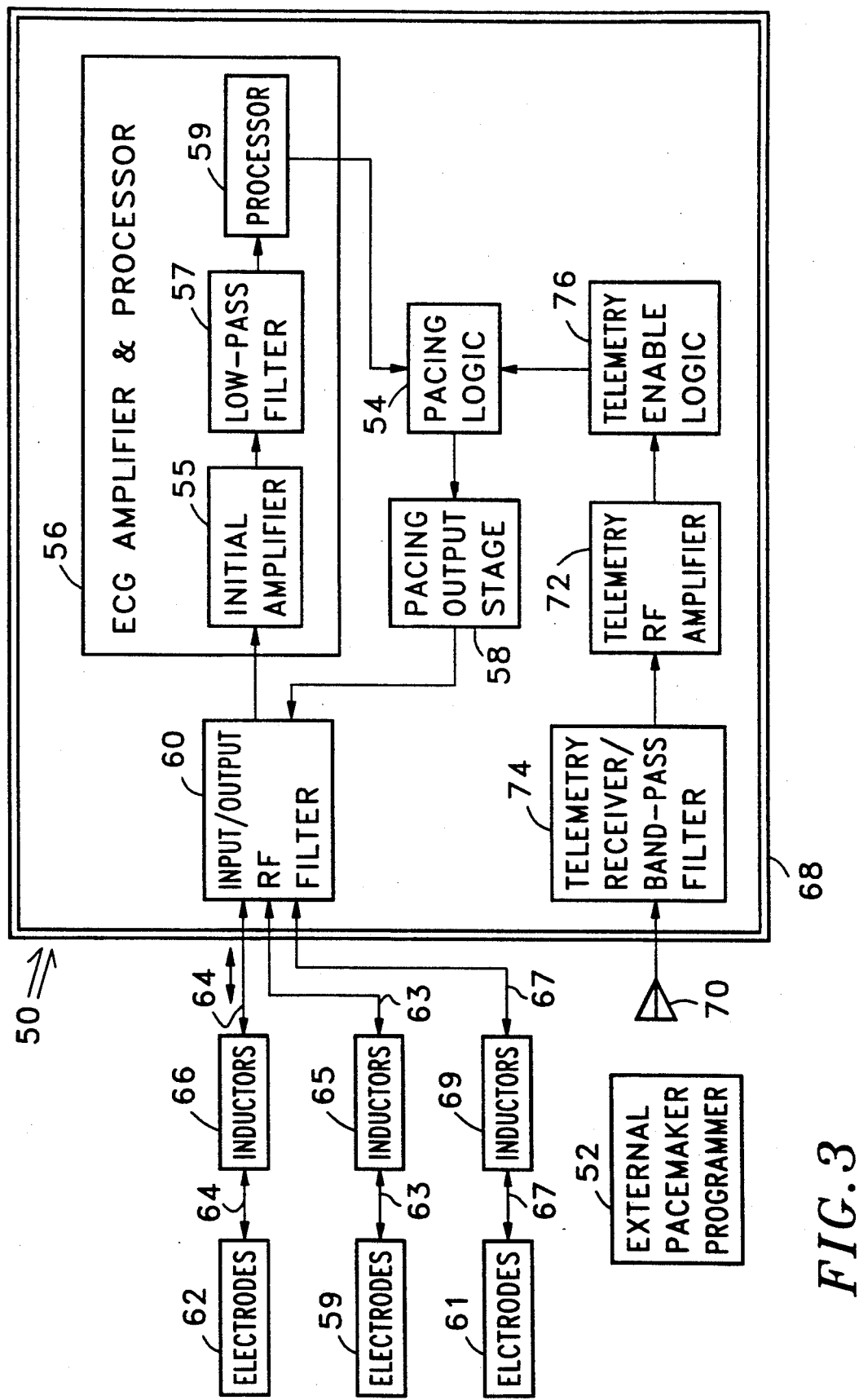
FIG. 3 is a block diagram of an invented implantable pacemaker, designed for external programming, which operates safely in the environment produced in an MRI system.

An implantable pacemaker 50 capable of bi-directional communication with an external programmer 52 is shown in FIG. 3. The implantable unit contains conventional programmable pacing logic 54 for sensing and/or pacing the ventricle and/or atrium and comprises: ECG amplifier and processor 56, pacing output stage 58, combined input/output RF filter 60, electrodes 62 and leads 64. The ECG amplifier and processor 56 contains a low-pass or band reject filter 57 placed after the initial amplifier 55 and before final stages 59. The low-pass or band reject filter must pass the QRS signals and reject gradient field frequencies caused by the MRI that are approximately 1–50 kHz. As in the previous embodiment, inductors 66 may be placed in the lead wires 64 close to the electrodes 62. (The electrodes 62, leads 64, inductors 66 and input/output filter 60 may be single elements performing combined input and output functions or may be separate input and output elements.) For dual chamber pacemakers, multiple sets of sensing/pacing electrodes may be used 59, 62, which are each connected to input/output RF filters 60. A first electrode pair may be for atrial sensing or pacing and a second electrode pair may be for ventricle sensing or pacing. As is taught in the pacing art, pacing logic 54 may be programmed, for example, to sense the atrial signal and pace via the ventricle electrodes. In addition, a new form of circulatory support called cardiomyoplasty may utilize other electrodes 61 and leads 67 to pace skeletal muscle wrapped around the heart and stimulated in synchrony with pacing the heart. In each type of pacemaker the leads 63, 64, 67 may contain inductors 65, 66, 69 to reduce electrical currents across the electrodes and each lead may be connected to separate input/output RF filter 60, as taught by this invention.

In order to protect the pacemaker from the effects of the RF field generated by the MRI system, it is necessary to surround the components with an RF shield 68. This shield may consist of a continuous, non-magnetic, metal case that prevents currents from being induced by the MRI system in the internal pacemaker circuitry. This shielding can be either a single layer or laminated case as later shown in FIG. 17.

Since the implantable pacemaker shown in FIG. 3 is enclosed in an RF shield, it was necessary to develop a unique method of external programming. The external programmer 52 works in a conventional manner. However, the information received by the pacemaker 50 is processed to separate the desired communication signal from the RF signals produced by the MRI system. An antenna 70 is connected to the telemetry RF amplifier 72 via the telemetry receiver/band pass filter 74. This filter is a band pass filter that passes only the specific programming frequency, currently approximately 100–200 kHz, to the telemetry amplifier 72. An algorithm in the telemetry logic circuit 76 interprets all RF received by the telemetry antenna 70 and will only allow programming of the pacing logic circuit 54 when a specific telemetry enable pattern is received. The telemetry enable logic circuit 76 will also inhibit control of the pacing output stage 58 while programming is taking place. This prevents improper and potentially dangerous pacing parameters from controlling the pacing stage. As a further safety measure, the telemetry enable circuit 76 enables pacing at a preset rate ("safety pacing") to provide adequate pacing back-up for pacemaker dependent patients during external programming.

FIGS. 4a–4f are schematic diagrams of the inductor elements (elements 20, 48, 50, 65, 66 and 69 in previous FIGS. 1 through 3) that are placed in the lead wires to reduce harmful currents. As mentioned previously, significant stray capacitance can be produced along the lead wires, particularly for external pacers. As a result, EMF generated between the electrodes because of the RF field can produce dangerously high currents flowing through the electrodes. To limit this current, and enhance patient safety, the inductor elements shown in FIGS. 4a–4f are placed in the lead wires close to the electrodes. FIG. 4a shows the inductor elements 78 when a two-wire lead is used; FIG. 4b shows the inductor elements 80 when a two-wire shielded lead is used; FIG. 4c shows alternative inductor elements 82, which incorporate a capacitor 84, thus comprising an additional low-pass L-C filter; FIG. 4d shows the same alternative inductor elements 83 and a capacitor 85, as shown in FIG. 4c, but using a shielded two-wire lead. FIG. 4e shows the inductor elements 86 used in a multi-lead shielded harness; and FIG. 4f shows alternative inductor elements 88 used in a multi-lead shielded harness, which also includes capacitor components 90 connected to the shielding enclosure of the capacitors. The leads can be used to measure ECG, EEG or other electrical signals of physiological significance. FIGS. 4a–4f show twisted leads, but it is to be understood that coaxial as well as other forms of lead wires could be used. Further, the leads should be made of non-magnetic materials to prevent physical motion of the wires caused by magnetic fields of the MRI system and distortion of the image by the wires.

FIGS. 5 through 9 and 14 through 16 show various embodiments of the input RF filter, output RF filter and combined input/output RF filter as taught by the present invention. According to the general principles taught by the present invention, there are many possible specific implementations of the RF filter design that will depend on: 1) whether two leads or multiple leads are used; 2) whether the leads are shielded; 3) whether single or multiple stage filtering is used; and, 4) whether each RF filter is housed in a separate shielded enclosure. It will also become apparent that the same filter design principles can be used whether the filter is acting as an input filter for an ECG monitor, as separate input filters and output filters for a pacemaker, or as a single combined input/output filter for a pacemaker.

Figure 5A:
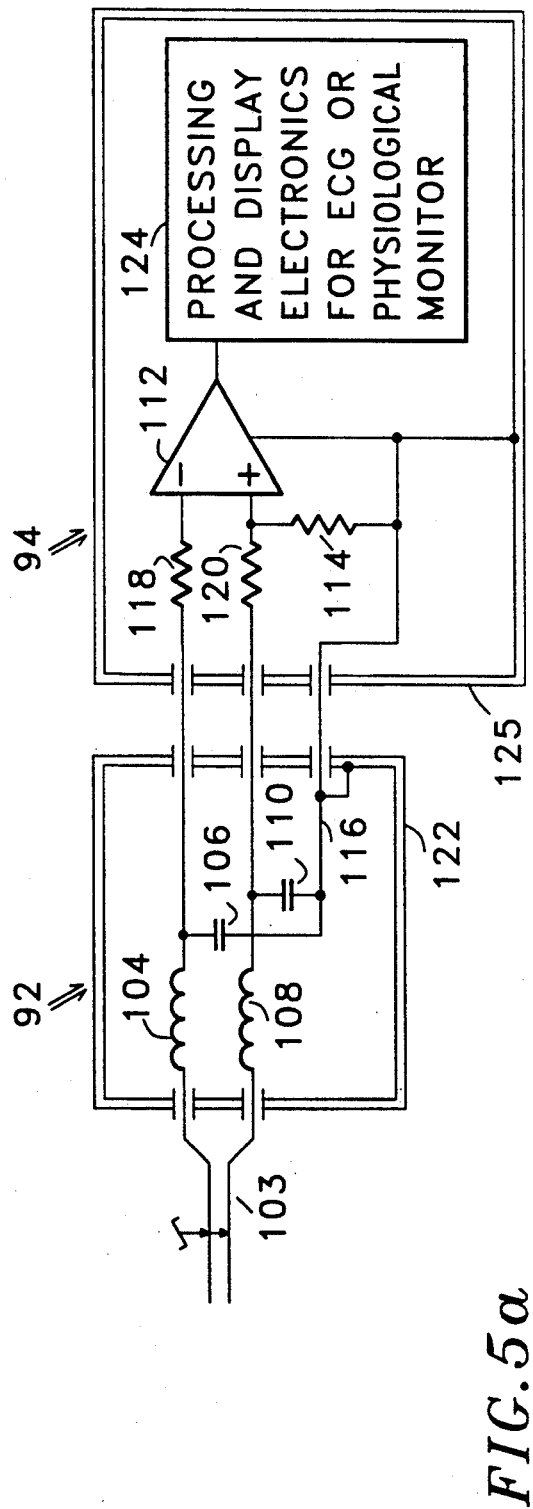
FIGS. 5a and 5b are block diagrams of ECG amplifiers with a one-stage RF filter design, as taught by the present invention, for use with dual unshielded leads.
Figure 5B:
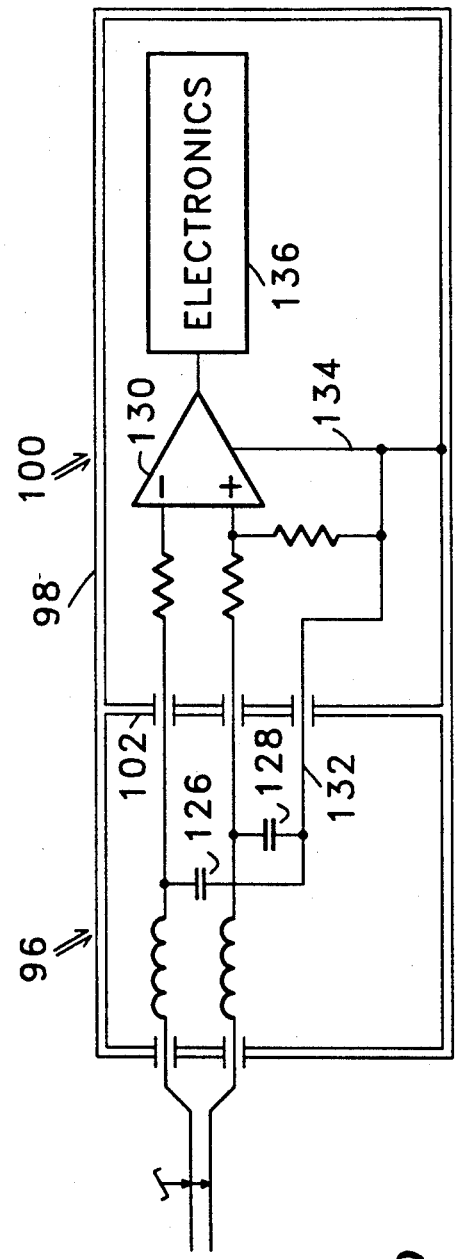

FIGS. 5a and 5b show one-stage filters, as taught by the present invention, for use with two unshielded leads. FIGS. 5a and 5b show alternative ways to shield the electronics. FIG. 5a shows the input filter 92 in a separate shielded enclosure; FIG. 5b shows the input filter 96 located in the same shielded enclosure 98 as the processing electronics 100 with an internal wall 102 shielding the monitoring electronics 100 from the input filter 96. (Whether one or two enclosures are used, the filter section should be shielded from the other circuitry.)

As can be seen in FIG. 5a, each lead is connected to a separate low-pass filter. (Leads 103 may be twisted to reduce electromagnetic interference). A first low-pass filter is made from inductor 104 and capacitor 106; and, a second low-pass filter is made from inductor 108 and capacitor 110. Each low-pass filter offers approximately 100 dB signal attenuation in the RF frequency range of the MRI system (generally 6–100 MHz) and passes with little attenuation the desired physiological signal (generally, 0–4 kHz). As mentioned previously, the L-C components must be high frequency elements retaining their desired characteristics throughout the 0–100 MHz frequency range. In addition, if the filter is included in an implantable device or exposed directly to the MRI system's magnetic fields, the inductors should not have ferromagnetic cores. The output from the input filter 92 is connected to differential amplifier 112. In order to properly utilize the differential amplifier 112, the non-inverting input of the ECG amplifier 112 is connected to the amplifier zero-signal reference terminal via a resistor 114, as is well known in the art. Obviously, any other method of converting a two to three conductor input may also be used. The two capacitors 106, 110 in the low-pass filters are referenced to a third wire 116 that is connected to the shield surrounding the filter 122 and also connected to the zero-signal reference terminal of the ECG amplifier 112. (As used throughout this specification (i.e. FIGS. 5–9 and 14–17) the ECG amplifier may be a single differential amplifier or a combination of multiple differential amplifiers, in addition the reference may be connected to a driven-right-leg arrangement, which is a well known common-mode interference reducing arrangement.) Alternatively, capacitors 106, 110 can be connected directly to the shield 122 with a separate wire connecting the shield 122 to the zero-signal reference terminal of the ECG amplifier 112. To improve the characteristics of the filter, resistors 118, 120 may be added between the input filter 92 and the input of the differential amplifier 112. Just as the input filter 92 is enclosed in a metallic shield 122, the ECG amplifier 112 and processor 124 may also be enclosed in a separate metallic shield 125. If the input filter or processor is in an implantable device or exposed directly to the MRI system's magnetic fields, the shield should be non-magnetic.

FIG. 5b shows an alternative embodiment where the input filter 96 and processing electronics 100 are housed in a single contiguous metallic shielding enclosure 98. For an implantable pacemaker, the case of the pacemaker can be isolated and laminated, as described in FIG. 17, to form the shield. A separate metallic wall 102 is used to shield the electronics 100 from the input filter 96. In the embodiment of FIG. 5b, the two capacitors 126, 128 that make up the low-pass filters are connected to the zero-signal reference terminal of the differential amplifiers 130 via a third reference wire 132; the reference wire 132 and zero-signal reference terminal 134 are both connected to the pacemaker shielding case at a single point.

Both FIGS. 5a and 5b show processing electronics 124, 136 that are used to further process the signal obtained from the differential amplifiers 112, 130. The processing electronics may be used to process and display the ECG signal, in the case of an external monitor, or be used to process and control pacing in the case of a pacemaker. It is to be understood that the invented filter embodiments shown in FIGS. 5a and 5b could be used in a device that monitors physiologically significant electrical signals other than ECG. (In all the embodiments shown in FIGS. 5–9, 14–16, if the filter and/or processing electronics are implanted or otherwise exposed to the MRI system's magnetic fields, the shielding enclosures should be made from a non-magnetic material and inductors used in the filter should not have ferromagnetic cores.)

FIGS. 6a and 6b show one-stage filter designs 135 and 137 that is preferred when the input leads are shielded. The design is identical to that shown in FIGS. 5a and 5b, except that the lead shield must be coupled to the shield enclosure via an RF filter. To accomplish this the lead shield 140 of the leads 138 in FIG. 6a is connected by an inductor 146 to the third reference wire 148, and the reference wire is connected to the filter's shielding enclosure 150. Analogously, the shield 144 of the leads 142 in FIG. 6b is connected by an inductor 154 to the reference wire 156, connected in turn to the enclosure 160.

In order to further reduce the effects of the MRI system RF signal, more than one stage of filtering can be used. In the embodiment shown in FIG. 7a, two stages of filtering are used. Each filter stage is similar to the filter described in FIG. 5a. Each input lead is connected to a low-pass filter. Each low-pass L-C filter has a capacitor connected to a reference wire which is connected to the shielding enclosure. The first stage filter 162 contains low-pass filters comprising inductors 164, 166 and capacitors 168, 170. Capacitors 168, 170 are coupled to a reference wire 172 which is connected to the enclosure 174. Similarly, the second filter stage 176 contains low-pass filters made from inductors 178, 180 and capacitors 182, 184, with capacitors 182, 184 coupled to the reference wire 172 which is connected to the shielding enclosure 177. All the capacitors (168, 170, 182 and 184) used in the low-pass filters are connected to the reference wire 172 which is connected to the zero-signal reference terminal of the differential amplifier 188. Each stage in FIG. 7a is housed in a separate shielding enclosure and each shielding enclosure is coupled to the reference wire 172. (It is understood that this concept can be extended to multistage filtering. The second stage 176 could actually represent the Nth stage of a multistage filter, with each identical stage coupled together as shown.)

An alternative embodiment for multiple stage filtering is shown in FIG. 7b. In this embodiment each filtering stage as well as the differential amplifier and the associated electronics are housed in the same contiguous shielding enclosure 192. The single case can be isolated and laminated as described in FIG. 17, with separate walls shielding the various filter stages from each other and from the amplifying and processing electronics. The filter design in this embodiment is identical to that shown in FIG. 7a; however, the reference wire is only connected to the shielding case 192 at a single point. (In effect, the low-pass filters in each stage and the zero-signal reference terminal of the differential amplifiers 194 are all referred to the same point on the shielding enclosure.) (It is to be understood that the embodiment shown in FIG. 7b may also have three or more stages, each stage shielded and coupled together as shown.)

FIGS. 8a and 8b are schematic drawings of a two-stage filter for use with shielded leads. These filters are similar to the multistage filter embodiments shown in FIGS. 7a and 7b, except that the lead shields are coupled via inductors to the reference wire in the last filter stage. FIG. 8a is a two-stage filter where each stage is separately isolated in metallic enclosures 196, 198. Again, as in the previous embodiments, low-pass filters are connected in each input lead and referenced to a common reference line 200 (i.e. capacitors 202, 204, 206 and 208 are connected to the reference line 200). The common reference line 200 is connected to the shielding enclosure for each stage and is input to the zero-signal reference terminal of the differential amplifier 210. The lead shield 212 is connected to inductor 214 in the first filter stage and via line 215 to inductor 216 in the second filter stage. The inductor 216 in the second, or final filter stage, is connected to the common reference line 200. As discussed previously, the inductors 214, 216 provide a high impedance to the undesirable high frequency RF voltages produced by the MRI system and prevent introduction of RF interference into the processing electronics via the common wire. (It is important to note that applicants have found it most desirable to connect the capacitors directly to zero-signal reference terminal via the reference line 200, as shown, and not via a line containing inductors.) To increase performance, an additional capacitor 218 may be connected between lines 215 and 200 in the first stage and any subsequent filter stage other than the last stage. Inductor 214 coupled with capacitor 218 provide a third low-pass filter.

FIG. 8b is a multistage filter housed in a single shielding enclosure 220 with separate walls 222, 224 isolating the filtering stages from each other and from the processing electronics. In the first stage 226, each lead 228 and the lead shield 230 are coupled to low-pass filters referenced by capacitors 230, 232, 234 to a common reference line 236. In the last stage 238, only the two lead wires contain low-pass filters referenced by capacitors 240, 242 to the common reference line 236. The lead shield 230 is coupled via inductor 244 directly to the reference line 236. As in the other embodiments, the reference line 236 is connected to the zero-signal reference terminal of the differential amplifier 248. Also as in the other embodiments, when a single case is used, the common reference line 236 is connected to the shielding enclosure at a single point.(It is of course understood that the two-stage filters shown in FIGS. 8a and 8b could be easily extended to multiple stage filtering with each stage connected as described.)

Figure 9A:
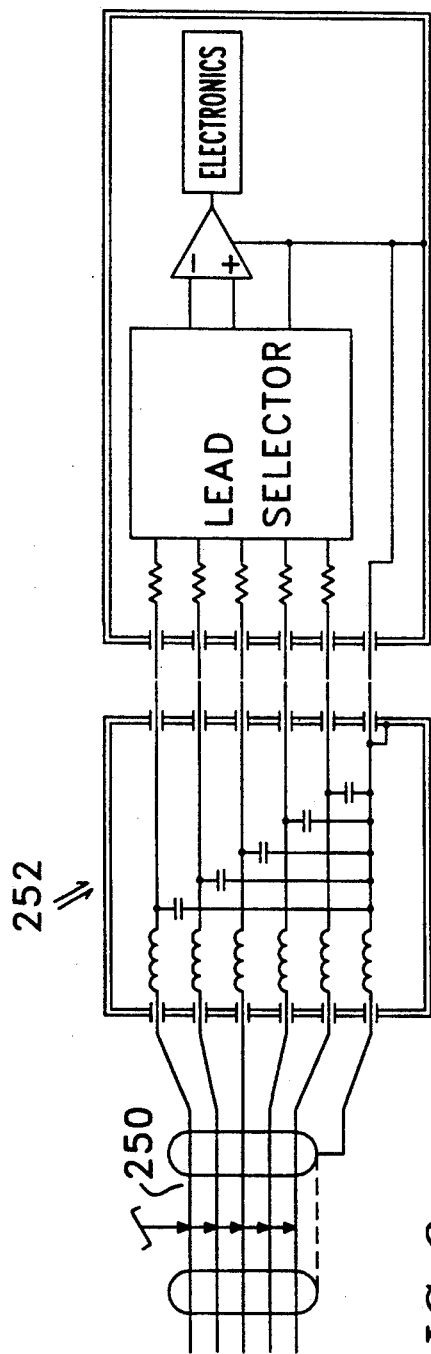
FIGS. 9a and 9b are block diagrams of ECG amplifiers with a multistage RF filter design, as taught by the present invention, for use with multilead ECG harness.
Figure 9B:
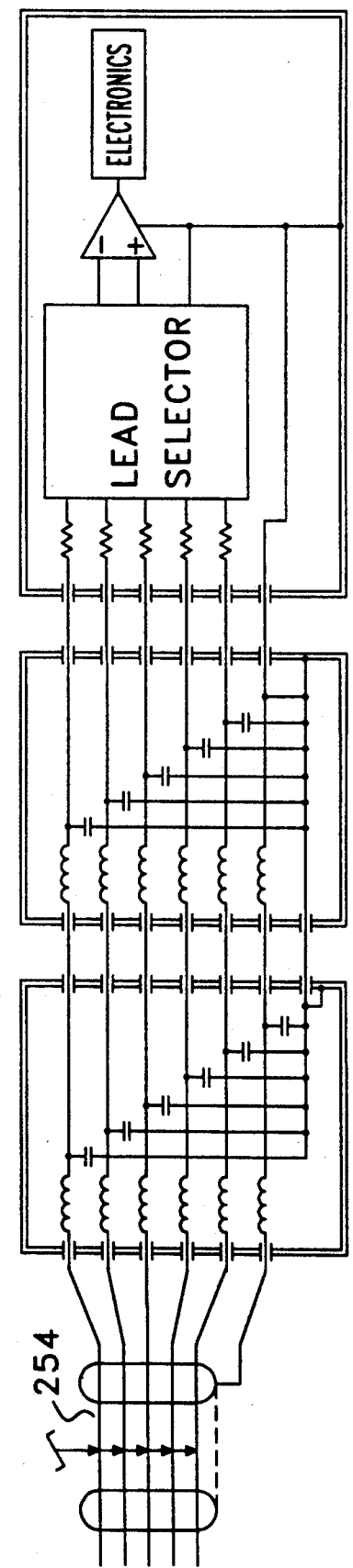

FIGS. 9a and 9b show an extension of the single and multiple stage filtering, as taught by the present invention to multiple lead shielded ECG harness. In FIG. 9a, a five conductor shielded cable 250 is filtered by a single stage filter 252 that is designed according to the invention taught herein. In FIG. 9b, a five conductor shielded cable 254 is filtered by a multiple stage filter 256 according to the invention taught herein.

Figure 10A:
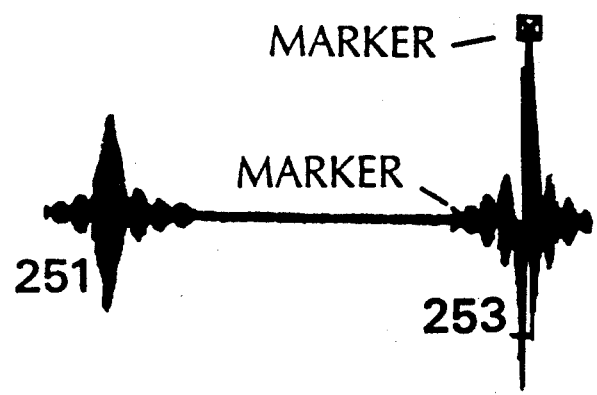
FIGS. 10a, 10b, 11a, 11b, 12a, 12b, 13a, 13b and 13c show recordings of the canine ECG using a digital storage oscilloscope.
Figure 10B:
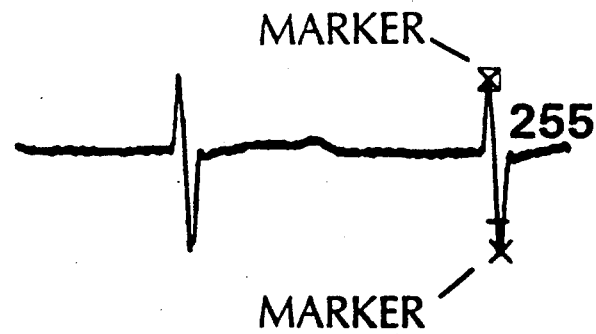

Experimental results obtained by the inventors clearly show the utility of the present invention. FIGS. 10a and 10b show the ECG signals obtained with a digital storage oscilloscope from three surface electrodes placed on a dog. Measurements were taken with the dog placed in an MRI System. As shown in FIG. 10a, the signal appearing on the ECG electrodes is dominated by the voltages induced by the RF pulses produced by the MRI system. The signal, shown as element 251, is produced by the 90° MRI pulse and the signal, shown as element 253 is the voltage produced by the 180° MRI pulse. (The paired 90° and 180° MRI RF pulses are used to generate the MRI image). The interfering signal appearing on the ECG lead is 34 volts peak-to-peak which completely masks the 6 mV peak-to-peak QRS signal. (On the scale used in FIG. 10a the QRS signal is below the noise level). Obviously, any pacing based on this input from the ECG leads would trigger at the MRI pulse rate, which would be too rapid and would jeopardize the patient. FIG. 10b, however, shows a very clear QRS signal after the invented RF filter. The voltages induced by the MRI RF pulses are attenuated and the desired 6 mV peak-to-peak QRS signal 255 is observed. Monitoring or pacing of the patient using this ECG signal can now safely proceed.

Figure 11A:
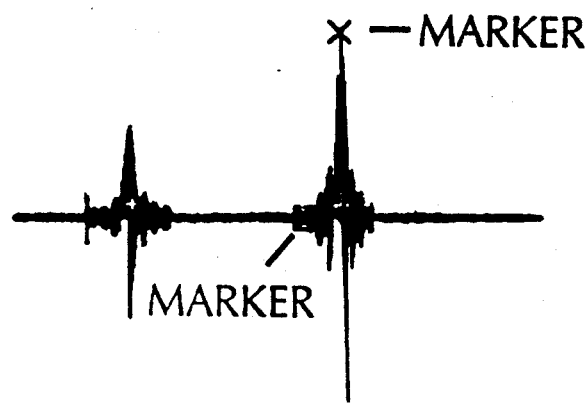
Figure 11B:
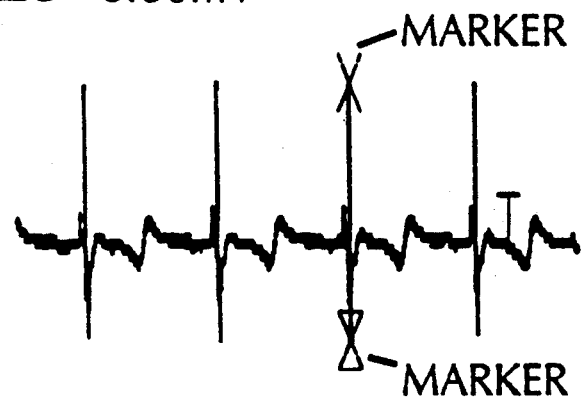

FIGS. 11a and 11b show the ECG signal obtained from electrodes implanted on the left ventricle surface of the dog. The dog was placed in the MRI system. As shown in FIG. 11a, the signal appearing on the electrodes is dominated by the voltages induced by the 90° and 180° MRI RF pulses. The interfering signal is 3.3 volts peak-to-peak and masks the desired QRS signal. Once the invented RF filter is used, as shown in FIG. 11b, the MRI induced RF signal is attenuated and only the lower 8.8 mV peak-to-peak QRS signal is observed. This QRS signal can be used for monitoring or pacing with complete patient safety.

Figure 12A:
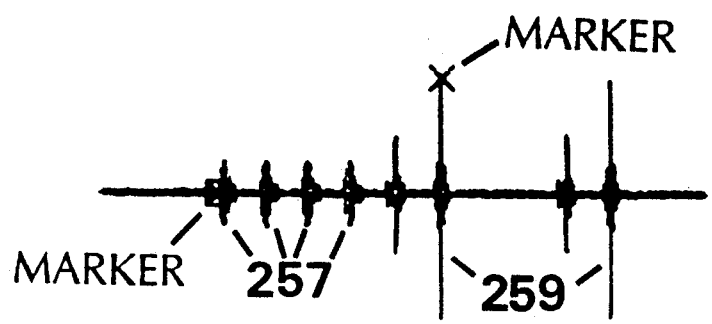
Figure 12B:
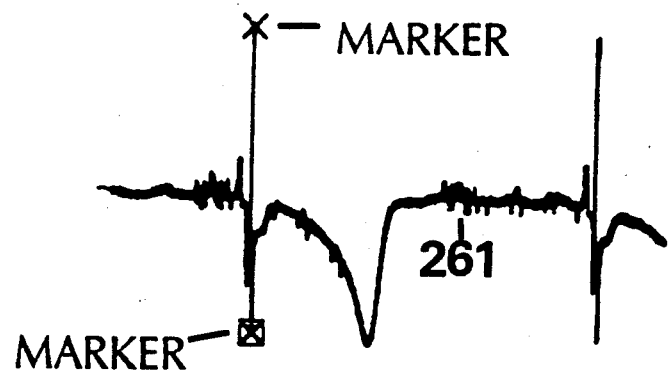

FIGS. 12a and 12b show the ECG signal obtained from implanted electrodes attached to the left ventricle surface of a dog. The dog is placed in an MRI system that uses four tag pulses 257 followed by two sets of 90° and 180° imaging pulses 259. Again, as shown in FIG. 12a, without the invented filtering technique the signal appear on the ECG electrode is dominated by the 3.8 volt peak-to-peak interfering signal. Pacing based on this signal would probably be fatal to the patient. However, application of the invented RF filter, as shown in FIG. 12b, eliminated the interfering signal and the 10.16 mV peak-to-peak QRS signal is observed. Additional noise 261 appears on the QRS signal which is caused by the MRI gradient filed. (This noise can be eliminated by using a low pass filter after the first amplifier stage as taught earlier in this Specification.)

Figure 13A:
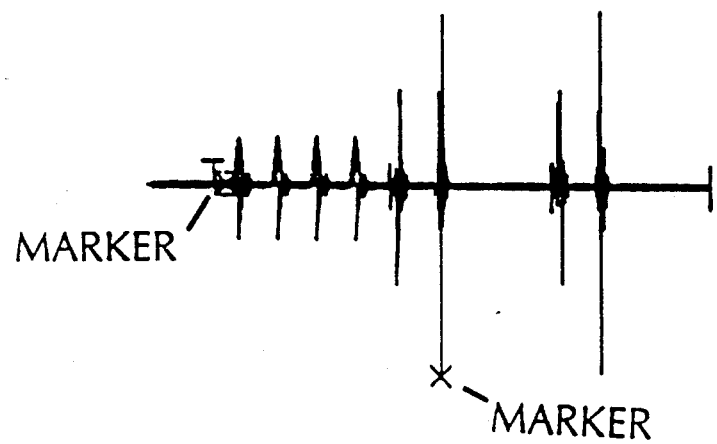
Figure 13B:
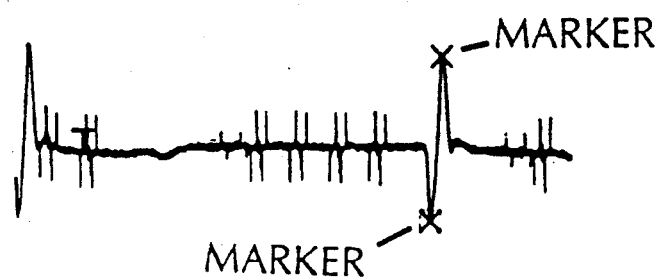
Figure 13C:
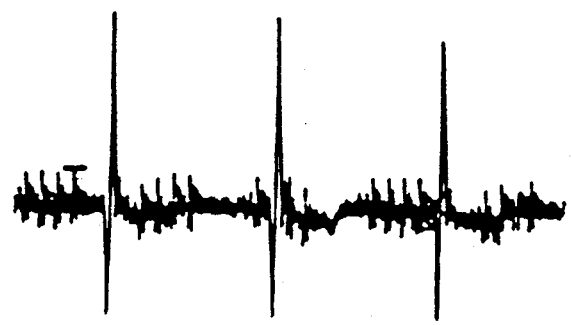

FIGS. 13a and 13b show the ECG signals obtained from three surface electrodes attached to a dog. The dog is placed in the MRI system producing four tag pulses followed by two sets of 90° and 180° imaging pulses. FIG. 13a shows the signal appearing prior to use of the invented RF filter. As can be seen from that figure, the 33 volt peak to peak interfering signal completely masks the desired QRS signal. FIG. 13b shows the signal recorded from the electrodes after the invented RF filtering is applied. The QRS signal is now clearly visible, although spikes caused by the MRI gradient magnetic field is also present. To eliminate these noise spikes, low-pass or band pass filter is placed after the first amplifier stage. This second filter passes the QRS signal but rejects the higher gradient field frequencies. FIG. 13c shows the ECG signal output after a low-pass filter having a frequency cut-off of 100 Hz is placed after the first amplifier stage. As shown in FIG. 13c a nicely shaped QRS signal results.

Obviously, the present invention has many possible embodiments with specific designs depending on whether single or multiple stage filters are used, whether double leads or multiple shielded leads are used and whether the leads are shielded. However, the general principles of the filter design are as follows: 1) each lead is separately filtered by a low-pass filter; 2) each low-pass filter is referenced by a capacitor to a common reference line;3) each filter stage should be surrounded by separate shielding enclosure (whether a single shielding case is used with separate isolated shielded compartments or whether separate shielding enclosures are used for each stage); 4) the common reference line can be connected to the zero-signal reference terminal of the differential amplifier and is connected to shielding enclosure (if separate shielding enclosures are used for each stage, the common reference is connected to each enclosure; if a single shielding case is employed the common reference line is connected to the enclosure at a single point); 5) the inductor and capacitor elements which make up the low-pass filter must be high frequency elements retaining their desired properties up to 100 MHz; and 6) each low pass filter must be designed to attenuate the high frequency RF voltages produced by the MRI system (in the range of 6-100 MHz) and pass the lower frequency desired physiological signals.

Figure 14:
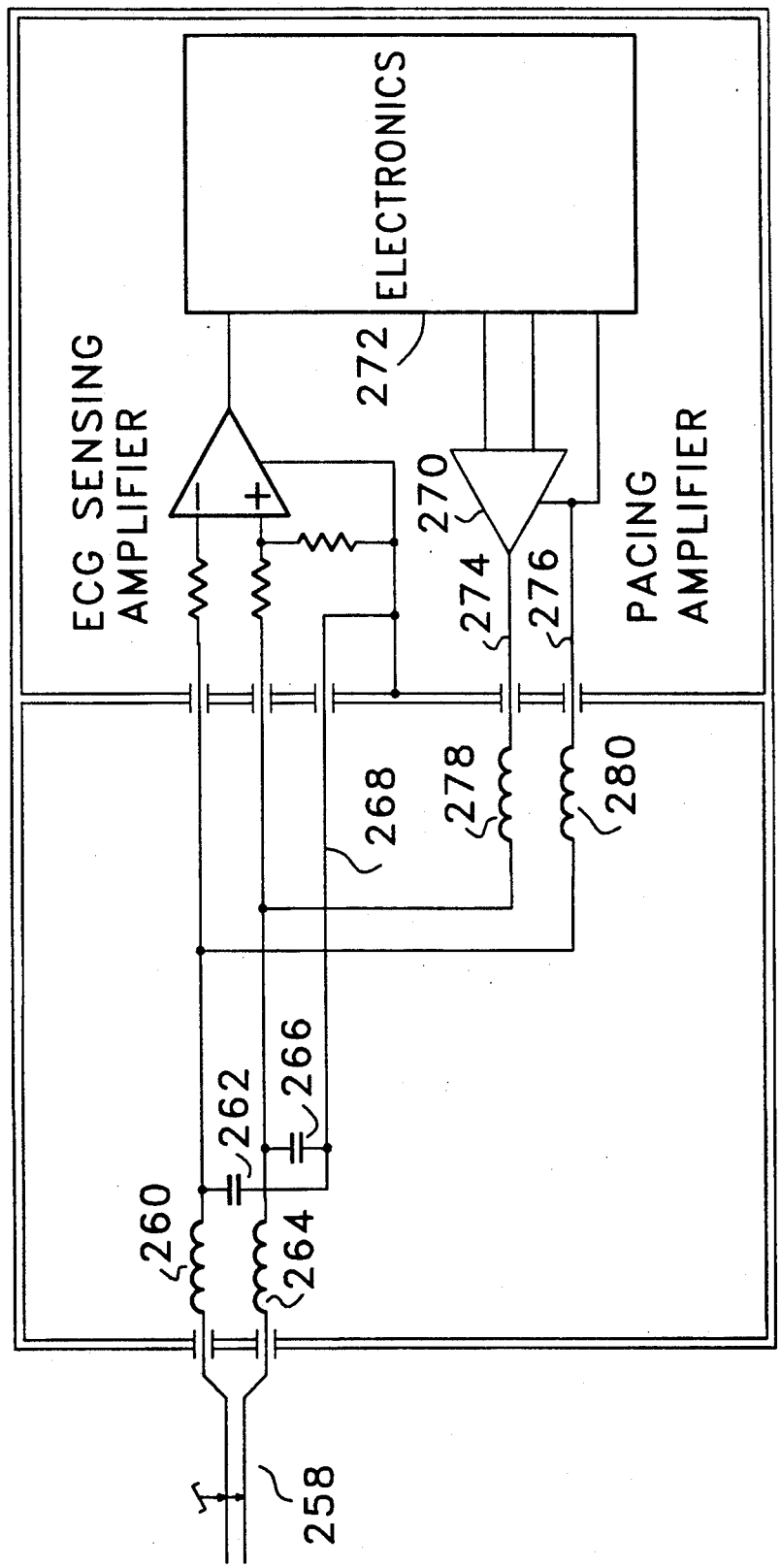
FIG. 14 is a block diagram of a MRI safe implantable pacemaker in accordance with the present invention.

Thus far, the invented filters have been described as input filters. However, as shown in FIG. 14, the invented filters can operate as both input and output filters. As generally true in pacemakers, the lead pair 258 can be used to sense electrical activity of the heart as well as to pace the heart. As shown previously, low pass filters (i.e. inductor 260/capacitor 262 pair and inductor 264/capacitor 266 pair) for each lead are referenced to a common reference line 268. The reference line 268 then connects to the zero-signal reference terminal of the differential amplifier and to the shielding enclosure. A pacing amplifier 270 in controlled by electronics 272 to generate a pacing signal. The pacing signal is connected via lines 274, 276 through the filter, to the leads 258. Two inductors 278, 280 are placed in lines 274, 276 to further prevent any current generated by the MRI system from affecting the pacing amplifier 270; the inductors 278, 280 provide an additional high impedance to the high frequency RF signals produced by the MRI system. Connecting the pacing amplifier to the leads 258 via the filter, as taught herein, can be used with each of the filter embodiments described in FIGS. 5 through 9. In multistage filtering embodiments, pacing amplifiers would be preferably connected into the last filtering stage.

Figure 15:
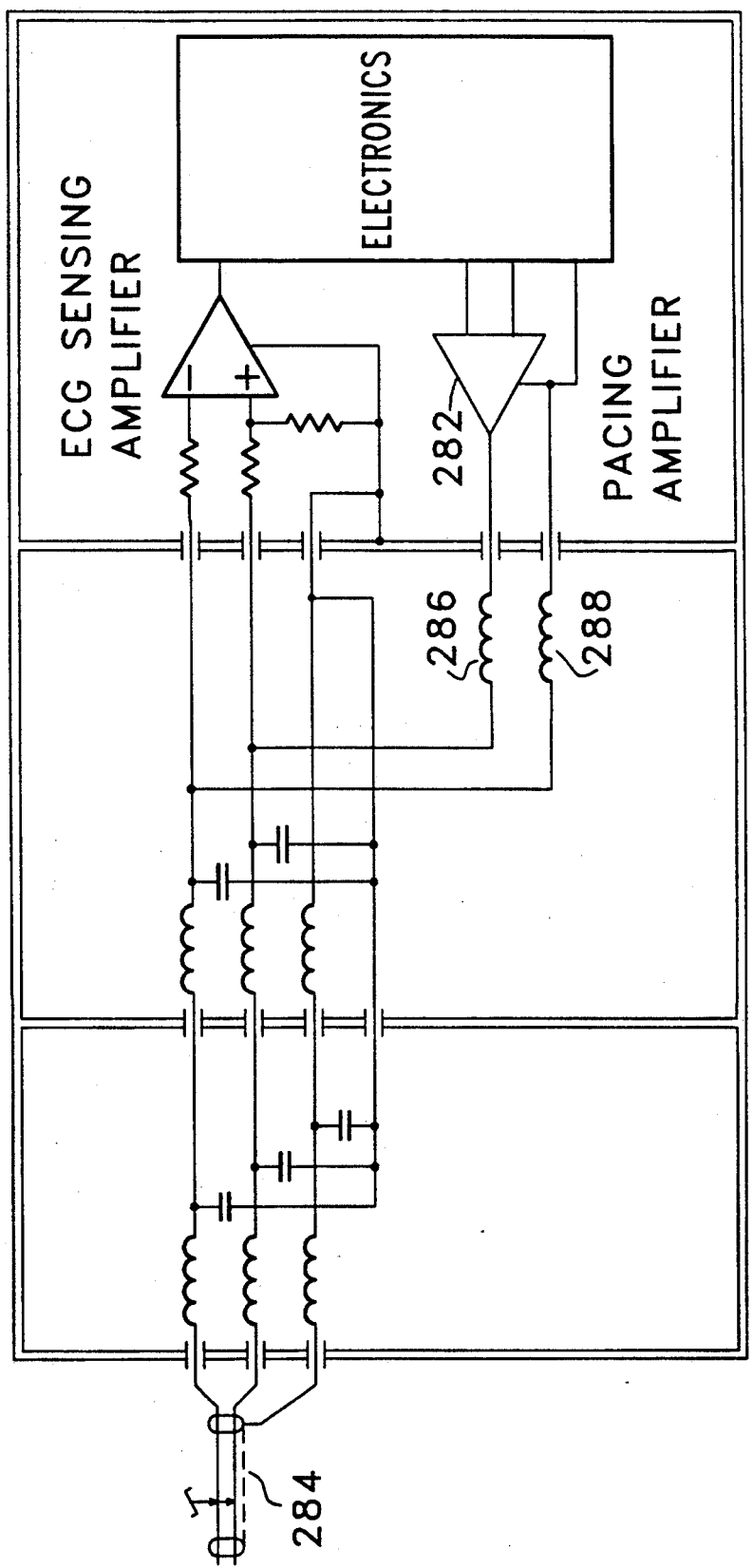
FIG. 15 is a block diagram of a MRI safe implantable pacemaker using a multistage RF filter, as taught by the present invention.

FIG. 15 is an exemplary embodiment, showing how the pacing amplifier 282 can be connected via a multistage filter to the shielded pacing/sensing leads 284. The pacing amplifier 282 is connected via inductors 286 and 288 to the lead wires in the last stage of the filter. As discussed above, the inductor 286, 288 provide additional protection from the high frequency RF signals generated by the MRI system.

Figure 16:
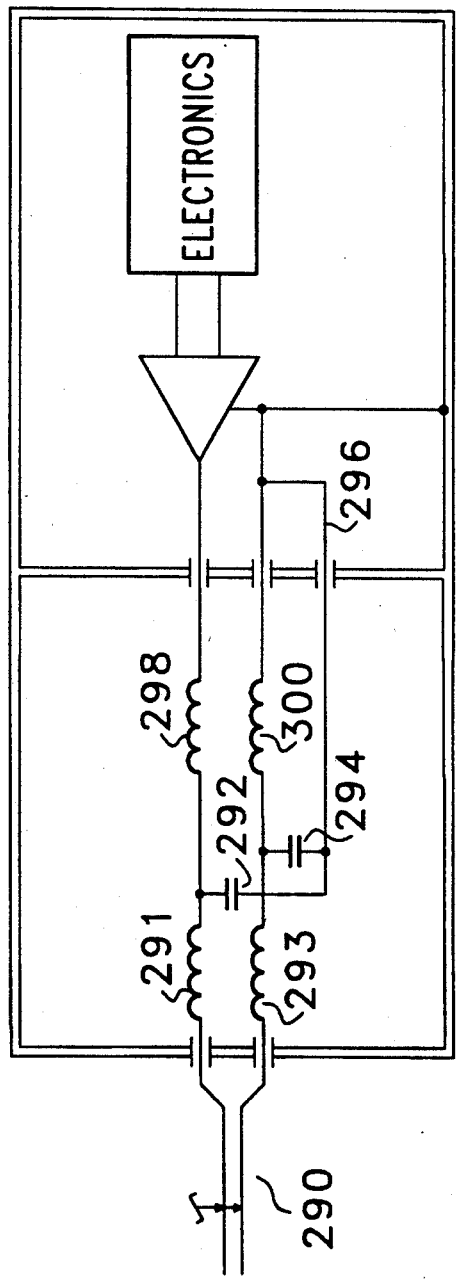
FIG. 16 is a block diagram of an implantable stimulator capable of operating in a MRI system, in accordance with the present invention.

Obviously, there are an unlimited number of ways in which the invented filters described herein can be connected to both sensing electronic and pacing amplifiers, which are within the contemplation of this invention. In fact, the same filter design can be used in stimulators, as shown in FIG. 16, where only a pacing signal is produced. The filter design is identical to those described previously in this specification. The leads 290 are each connected to low pass filters (inductor 291/capacitor 292 pair and inductor 293/capacitor 294 pair) that are referred by capacitors 292, 294 to a common reference line 296. Inductors 298, 300 provide additional isolation to protect the pacing amplifier. Obviously, the filter design for stimulation use only can be extended to multistage embodiments as taught previously in FIGS. 7 through 9.

Figure 17:
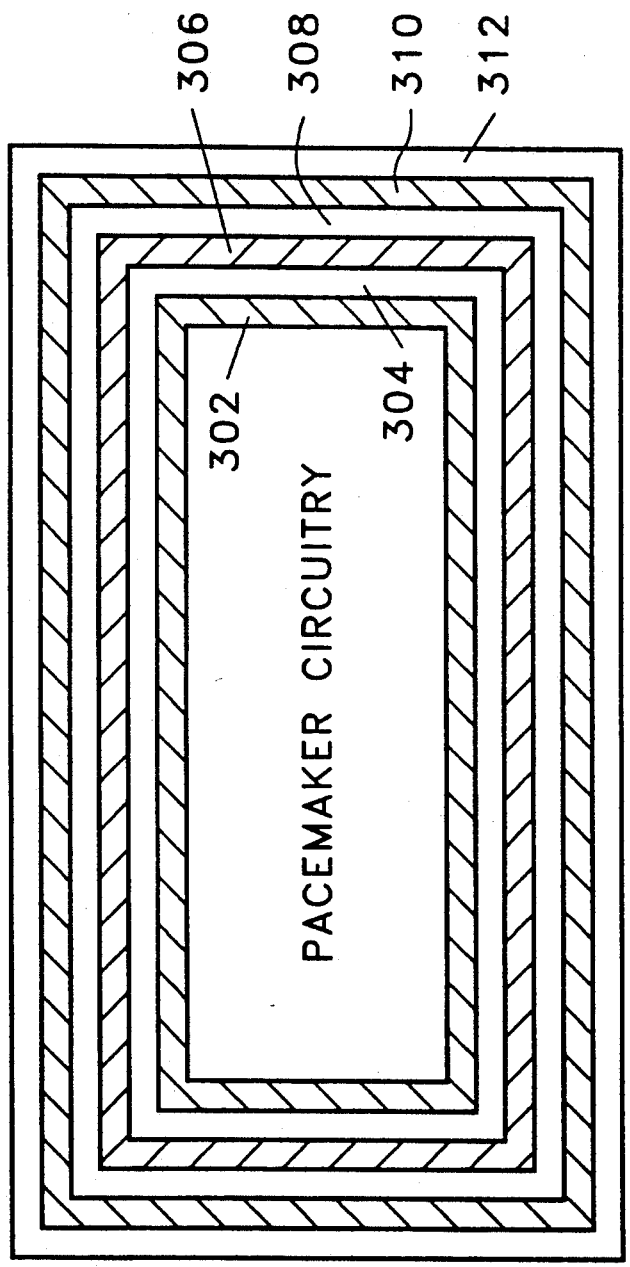
FIG. 17 is a cross-section of a laminated enclosure used in an implantable pacemaker, as taught by the present invention.

In order to protect the implantable pacemaker elements from the effects of the RF signals produced by the MRI system, it is necessary to surround the components with an RF shield. This shielding will consist of a continuous, non-magnetic, metal case that prevents currents from being induced inside the internal pacemakers circuitry. This shielding can be either a single layer or a laminated case, as shown in FIG. 17. The laminated implantable pacemaker case can contain alternating metal and insulating layers. As shown in FIG. 17, layers 302, 306, 310 are metal and layers 304, 308, and 312 are insulating. This embodiment will reduce heating and other interference with proper pacemaker function caused by current flowing between the pacing/sensing electrodes and the case of the pacemaker. Obviously, any reasonable number of laminated layers can be used to achieve this affect.

Obviously, many modifications and variations of the present invention are possible in light of the above teachings. It is, therefore to be understood that within the scope of the appended claims, the invention may be practiced otherwise than as specifically described.

What is claimed and desired to be secured by Letters Patent of the United States is:

1. A device for amplifying an electrical signal of physiological significance that can operate in a high radio frequency (RF) environment produced in a magnetic resonance imaging apparatus, said device comprising:
    at least two electrodes with associated input leads for coupling to a patient;
    an amplifier means having a zero-signal reference terminal for detecting and amplifying the desired physiological signal; and,
    a filter means, connected to said input leads and coupling said at least two electrodes to said amplifier means, for attenuating any induced RF signal produced by said imaging apparatus and passing the lower frequency desired electrical physiological signal, said filter means including:
    a conductive shield enclosing said filter means,
    a common reference line coupled to said conductive shield enclosure at one point and to the zero-signal reference terminal of said amplifier;
    at least two low pass filters, each connected to one of said input leads and each of said at least two low pass filters referenced to said common reference line.

2. The device of claim 1, wherein said conductive shield surrounding said filter means is made from non-magnetic material.

3. A device for amplifying an electrical signal of physiological significance that can operate in a high radio frequency (RF) environment produced in a magnetic resonance imaging apparatus, said device comprising:
    at least two electrodes with associated input leads for coupling to a patient
    an amplifier means having zero-signal reference terminal for detecting and amplifying a desired physiological signal; and,
    a filter means, connected to said input leads and coupling said at least two electrodes to said amplifier means, for attenuating any induced RF signal produced by said imaging apparatus and passing the lower frequency desired electrical physiological signal, said filter means including:
    a conductive housing enclosing said filter means and said amplifier means, said conductive housing having a second shielding means for shielding said amplifier means from said filter means,
    a common reference line coupled to said conductive housing at one point and to the zero-signal reference terminal of said amplifier, and at least two low pass filters, each connected to one of said input leads and each of said at least two low pass filters referenced to said common reference.

4. The device of claim 3, wherein said second shielding means is a separate compartment within said conductive housing having a wall for separating said filter means from said amplifier means.

5. The device of claim 3, wherein said conductive housing is made from non-magnetic material.

6. The device of claim 1 or 3, wherein each of said at least two low pass filters comprises an inductor coupling one of the said input leads to said amplifier means, and a capacitor connected to said common reference line.

7. The device of claim 6, wherein said input leads have a common shield and wherein said shield is coupled to said common reference line through an inductor.

8. The device of claim 6, wherein said inductors and capacitors are high frequency components.

9. The device of claim 1 or 3 wherein said device for amplifying is connected to control electronics and wherein said control electronics is connected to a pacing circuit.

10. The device of claim 1 or 3, wherein each of said input leads contains an inductor means placed in said input lead close to said electrode, for reducing currents harmful to the patient.

11. The device of claims 1 or 3, further comprising a second filter means, connected to the output of said amplifier means, for passing the lower frequencies desired physiological signal and rejecting the higher frequency signal produced by the imaging apparatus gradient field.

12. The device of claim 11, wherein said second filter means is a low pass filter.

13. The device of claim 11, wherein said second filter means is a band reject filter.

14. The device of claim 11, wherein said second filter means rejects frequencies above 1 kHz.

15. The device of claims 1 or 3, wherein said filter means attenuates frequencies from 6-100 mHz.

16. A device for amplifying an electrical signal of physiological significance that can operate in a high radio frequency (RF) environment produced in a magnetic resonance imaging apparatus, said device comprising:

at least two electrodes with associated input leads for coupling to a patent;
an amplifier means having a zero reference terminal for detecting and amplifying the desired electrical physiological signal; and,
a filter means comprising a series of n filter stages, wherein n is greater than one, wherein said first stage connects by said input leads to said at least two electrodes and said nth stage connects to said amplifier means, and wherein each filter stage connects in series between said first and nth stages for attenuating the RF signal produced by an imaging apparatus and passing the lower frequency desired electrical physiological signal, each filter stage including:
a conductive shield enclosing said filter stage,
a common reference line connected to said conductive shield enclosure at one point and wherein said common reference line also connects in series each shield enclosure associated with each filter stage and to the zero-signal reference terminal of said amplifier; and,
at least two low pass filters, each of said two low pass filters referenced to said common reference line.

17. The device of claim 16, wherein said conductive shield surrounding each filter stage is made from non-magnetic material.

18. The device of claim 16 wherein said conductive housing has laminated layers of alternating conductive and insulating material, wherein the external layer is insulating.

19. A device for amplifying an electrical signal of physiological significance that can operate in a high radio frequency (RF) environment produced in a magnetic resonance imaging apparatus, said device comprising:

at least two electrodes with associated input levels for coupling to a patent;
an amplifier means having a zero reference terminal for detecting and amplifying the desired electrical physiological signal;
a conductive housing enclosing said device, including said amplifier means and said filter means, with separate shielding means for shielding said filter means from said amplifier means;
a filter means comprising a series of n filter stages, wherein n is greater than one, wherein said first stage connects by said input leads to said at least two electrodes and said nth stage connects to said amplifier means, and wherein each filter stage connects in series between said first and nth stages for attenuating the RF signal produced by imaging apparatus and passing the lower frequency desired electrical physiological signal, each filter stage including;
a common reference line connected to said conductive housing at one point and to the zero-signal reference terminal of said amplifier means, and
at least two low pass filters, each of said two low pass filters referenced to said common reference line.

20. The device of claim 19, wherein said separate shielding means shields each filter stage from the other filter stages and from the amplifier means.

21. The device of claim 20, wherein said separate shield means is a series of separate compartments within said conductive housing having walls for separating each of said filter stages from each other and from the amplifier means.

22. The device of claim 19, wherein said conductive housing is made from non-magnetic material.

23. The device of claim 16 or 19, wherein said input leads are shielded and wherein an additional lead wire extends from said shield and is coupled in series to each filter stage, and wherein each filter stage except the nth filter stage further contains a low pass filter connected to said additional lead wire and is referenced to said common reference line, and wherein in said nth filter stage said additional lead wire is connected to said common reference line by an inductor.

24. The device of claim 16 or 19 wherein each of said at least two low pass filters comprises an inductor and a capacitor, wherein said capacitor is referenced to said common reference line.

25. The device of claim 24, wherein said inductors and capacitors are high frequency components.

26. The device of claim 16 or 19, wherein said device for amplifying is connected by control electronics to a pacing circuit.

27. The device of claim 16 or 19, wherein each of said input leads contains an inductor means placed in a said input lead close to said electrode, for reducing currents harmful to the patient.

28. The device of claim 16 or 19, further comprising a second filter means, coupled to the output of said amplifier means, for passing the lower frequency desired physiological signal and rejecting the higher frequency signal produced by the imaging apparatus gradient field.

29. The device of claim 28, wherein said second filter means is a low pass filter.

30. The device of claim 28, wherein said second filter means is a band reject filter.

31. The device of claim 28, wherein said second filter means rejects frequencies above 1 kHz.

32. The device of claim 16 or 19, wherein said filter means attenuates frequencies from 6–100 mHz.

33. An implantable pacemaker that can operate in a high radio frequency (RF) environment produced in a magnetic resonance imaging apparatus, said pacemaker comprising:
   at least two electrodes for implantation in a patient;
   a cable containing at least two leads electrically coupled to said at least two electrodes;
   a pacemaker circuit comprising a sensing amplifier having a zero-signal reference terminal, a pacing amplifier and control electronics;
   a filter means coupling said leads to said sensing amplifier, for attenuating any induced RF signal produced by said imaging apparatus and passing the lower frequency desired electrical physiological signal, said filter means comprising a series of n filter stages, wherein each filter stage includes at least two low pass filters, each low pass filter couples to one of said leads and all of said low pass filters are referenced to a common reference, said common reference connected to the zero-signal reference terminal of said sensing amplifier, and wherein an additional lead connected to said cable shield is coupled in series to each filter stage, wherein each filter stage except the nth filter stage further contains a low pass filter connected to said additional lead and referenced to said common reference, and wherein in said nth filter stage said additional lead is connected to said common referenced by an inductor;
   an inductor coupling means for coupling output from said pacing amplifier to said at least two leads for producing an additional high impedance to the RF signals produced by the imaging apparatus; and,
   a conductive housing enclosing said pacemaker, including said electronic circuit, filter means and inductor coupling means, with a second shielding means for shielding each filter stage from said inductor electronic circuit, said common reference being connected to said conductive housing at one point.

34. The pacemaker of claim 33, wherein said conductive housing is laminated containing alternating conductive and insulating layers to reduce heating produced by the imaging apparatus RF signal.

35. An implantable pacemaker that can operate in a high radio frequency (RF) environment produced in a magnetic resonance imaging apparatus, said pacemaker comprising:
   at least two electrodes for implantation in a patient;
   a shielded cable containing at least two leads electrically coupled to said at least two electrodes;
   an electronic circuit comprising a sensing amplifier having a zero-signal reference terminal, a pacing amplifier and control electronics;
   a filter means coupling said leads to said sensing amplifier terminal, for attenuating any induced RF signal produced by said imaging apparatus and passing the lower frequency desired electrical physiological signal, said filter means comprises a series of n filter stages, where n is greater than one, wherein each filter stage includes at least two low pass filters, each low pass filter couples to one of said leads and all of said low pass filters are referenced to a common reference line, said common reference line connected to the zero-signal reference terminal of said sensing amplifier, and wherein an additional lead connected to said cable shield is coupled in series to each filter stage, wherein each filter stage except the nth filter stage further contains a low pass filter connected to said additional lead and referenced to said common reference line, and wherein in said nth filter stage said additional lead is connected to said common reference line by an inductor;
   an inductor coupling means for coupling output from said pacing amplifier to said at least two leads for producing an additional high impedance to the RF signals produced by the imaging apparatus; and,
   a conductive housing enclosing said pacemaker, including said electronic circuit, filter means and inductor coupling means, with a second shielding means for shielding each filter stage from said electronic circuit, said common reference line being connected to said conductive housing at one point.

36. The pacemaker of claim 35, wherein said conductive housing is laminated containing alternating conductive and insulating layers to reduce heating produced by the imaging apparatus RF signal.

37. An implantable stimulator that can operate in a high radio frequency (RF) environment produced in a magnetic resonance imaging apparatus, said stimulator comprising:
   at least two electrodes with associated input leads for implantation in a patient;
   an electronic circuit to generate the stimulation signal;
   a common reference line;
   a filter means connected to said leads and coupling said at least two electrodes to said electronic circuit for providing a high impedance to any RF signal produced by the imaging apparatus, said filter means comprises at least two low pass filters, each connected to one of said leads and each of said at least two low pass filters referenced to said common reference line;
   an inductor coupling means for coupling output from said electronic circuit to said filter means for producing additional high impedance to the RF signals produced by the imaging apparatus; and,
   a conductive housing enclosing said stimulators, including said electronic circuit, filter means and inductor coupling means, with a second shielding means for shielding said filter means and said inductor coupling means from said electronic circuit, said common reference line being connected to said conductive housing at one point.

38. The stimulator of claim 37, wherein said conductive housing is laminated containing alternating conductive and insulating layers to reduce heating produced by the imaging apparatus RF signal.

* * * * *